US006812021B1

(12) United States Patent
Hughes et al.

(10) Patent No.: US 6,812,021 B1
(45) Date of Patent: Nov. 2, 2004

(54) GENES AND PROTEINS AND THEIR USE

(75) Inventors: Martin John Glenton Hughes, Berkshire (GB); Joseph David Santangelo, Berkshire (GB); Jonathan Douglas Lane, Berkshire (GB); Robert Feldman, Berkshire (GB); Joanne Christine Moore, Berkshire (GB); Richard James Dobson, Berkshire (GB); Paul Everest, Dumbartonshire (GB); Gordon Dougan, London (GB); Rebecca Kerry Wilson, London (GB)

(73) Assignee: Microscience Limited (GB)

( * ) Notice: Subject to any disclaimer, the term of this patent is extended or adjusted under 35 U.S.C. 154(b) by 0 days.

(21) Appl. No.: 09/868,352

(22) PCT Filed: Dec. 22, 1999

(86) PCT No.: PCT/GB99/04377

§ 371 (c)(1),
(2), (4) Date: Sep. 10, 2001

(87) PCT Pub. No.: WO00/37646

PCT Pub. Date: Jun. 29, 2000

(30) Foreign Application Priority Data

| Dec. 22, 1998 | (GB) | ............................................. | 9828345 |
|---|---|---|---|
| Dec. 22, 1998 | (GB) | ............................................. | 9828349 |
| Dec. 22, 1998 | (GB) | ............................................. | 9828350 |
| Dec. 22, 1998 | (GB) | ............................................. | 9828352 |
| Dec. 22, 1998 | (GB) | ............................................. | 9828353 |
| Dec. 22, 1998 | (GB) | ............................................. | 9828354 |
| Dec. 22, 1998 | (GB) | ............................................. | 9828355 |
| Dec. 22, 1998 | (GB) | ............................................. | 9828356 |
| Dec. 22, 1998 | (GB) | ............................................. | 9828357 |
| Dec. 22, 1998 | (GB) | ............................................. | 9828359 |
| Jan. 4, 1999 | (GB) | ............................................. | 9900082 |
| Jan. 4, 1999 | (GB) | ............................................. | 9900083 |
| Jan. 4, 1999 | (GB) | ............................................. | 9900084 |
| Jan. 4, 1999 | (GB) | ............................................. | 9900085 |
| Jan. 4, 1999 | (GB) | ............................................. | 9900086 |
| Jan. 28, 1999 | (GB) | ............................................. | 9901916 |
| Jan. 28, 1999 | (GB) | ............................................. | 9901922 |

(51) Int. Cl.[7] .......................... C12N 1/20; C12N 15/00; C12N 5/00; C12P 21/06; C07H 21/04
(52) U.S. Cl. .............. 435/252.3; 435/69.1; 435/252.33; 435/252.4; 435/320.1; 424/190.1; 536/23.7
(58) Field of Search ........................ 435/252.3, 252.33, 435/252.4, 320.1, 69.1, 69.3, 253.4, 243, 91.1; 424/190.1, 184.1, 185.1, 244.1; 536/23.7, 23.1, 24.3, 24.32

(56) References Cited

FOREIGN PATENT DOCUMENTS

WO          0006736       7/1999

OTHER PUBLICATIONS

Ellis, R.W. (Chapter 29 of "VACCINES" Plotkin, 5.A. et al. (eds) published by W. B. Saunders company (Philadelphia) in 1988,.*

Rudinger et al, in "Peptide Hormones", edited by Parsons, J.A., University Park Press, Jun. 1976, p. 6.*

Burgess et al., The Journal of Cell Biology, 111:2129–2138, 1990.*

Lazar et al., Molecular and Cellular Biology, 8(3): 1247–1252, 1988.*

Jobling et al. (Mol. Microbiol. 1991, 5(7): 1755–67.*

Larsson, Charlotte, Margaretha Ståhammar–Carlemalm, Gunnar Lindahl (Sep. 1996) "Experimental Vaccination Against Group B Streptococcus, an Encapsulated Bacterium, with Highly Purified Preparations of Cell Surface Proteins Rib and α" *Infection and Immunity* 64(9):3518–3523.

Wastfelt, Maria, Margaretha Stalhammar–Carlemalm, Anne–Marie Delisse et al. (Aug. 1996) "Identification of a Family of Streptococcal Surface Proteins with Extremely Repetitive Structure" *The Journal of Biological Chemistry* 271(31):18892–18897.

Giffard, Philip M., Catherine Rathsam, Edward Kwan et al. (1993) "The ftf gene encoding the cell–bound fructosyl–transferase of *Streptococcus salivarius* ATCC 25975 is preceded by an insertion sequence and followed by FUR1 and clpP homologues" *Journal of General Microbiology* 139:913–920.

Giffard, Philip M. et al. Sequence ID CLPP_STRSL, Jun. 1, 1994, EMBL Database Accession no P36398.

Maurizi, Michael R., William P. Clark, Yoko Katayama et al. (Jul. 1990) "Sequence and Structure of Clp P, the Proteolytic Component of the ATP–dependent Clp Protease of *Escherichia coli*" *The Journal of Biological Chemistry* 265(21):12536–12545.

Tsukioka, Yuichi, Yoshihisa Yamashita, Takahiko Oho et al. (Feb. 1997) "Biological Function of the dTDP–Rhamnose Synthesis Pathway in *Streptococcus mutans*" *Journal of Bacteriology* 179(4):1126–1134.

Yuichi, Tsukioka et al., Sequence ID P95779, May 1, 1997, EMBL Database Accesssion no P95779.

Coffey, T. et al. (Jun. 1998) "Recombinational exchanges at the capsular polysacchairde biosynthesis locus . . . " *Molecular Microbiology* 27:73–83; EMBL Database Accession No. 054547 Sequence ID 054547. Sequence only.

* cited by examiner

*Primary Examiner*—Lynette R. F. Smith
*Assistant Examiner*—Padma Baskar
(74) *Attorney, Agent, or Firm*—Saliwanchik, Lloyd & Saliwanchik

(57) ABSTRACT

According to the present invention, a series of genes are identified in Group B Streptococcus, the products of which may be associated with the outer surface of the organism. The genes, or functional fragments thereof, may be useful in the preparation of therapeutics, e.g. vacaccines to immunize a patient against microbial infection.

8 Claims, No Drawings

GENES AND PROTEINS AND THEIR USE

This application is a National Stage Application of International Application Number PCT/GB99/04377, filed Dec. 22, 1999.

FIELD OF THE INVENTION

This invention relates to the identification of bacterial genes and proteins, and their use. More particularly, it relates to their use in therapy, for immunisation and in screening for drugs.

BACKGROUND TO THE INVENTION

Group B Streptococcus (GBS), also known as *Streptococcus agalactiae*, is the causative agent of various conditions. In particular, GBS causes:
Early Onset Neonatal Infection.

This infection usually begins in utero and causes severe septicaemia and pneumonia in infants, which is lethal if untreated and even with treatment is associated with a 10–20% mortality rate.
Late Onset Neonatal Infection.

This infection occurs in the period shortly after birth until about 3 months of age. It causes a septicaemia, which is complicated by meningitis in 90% of cases. Other focal infections also occur including osteomyelitis, septic arthritis, abscesses and endopthalmitis.
Adult Infections.

These appear to be increasingly common and occur most frequently in women who have just delivered a baby, the elderly and the immunocompromised. They are characterised by septicaemia and focal infections including osteomyelitis, septic arthritis, abscesses and endopthalmitis.
Urinary Tract Infections.

GBS is a cause of urinary tract infections and in pregnancy accounts for about 10% of all infections.
Veterinary Infections.

GBS causes chronic mastitis in cows. This, in turn, leads to reduced milk production and is therefore of considerable economic importance.

GBS infections can be treated with antibiotics. However, immunisation is preferable. It is therefore desirable to develop an immunogen that could be used in a therapeutically-effective vaccine.

SUMMARY OF THE INVENTION

The present invention is based on the identification of a series of genes in GBS, and also related organisms, the products of which may be localised on the outer surface of the organism and therefore may be used as a target for immuno-therapy.

According to one aspect of the invention, a peptide is encoded by an operon including any of the genes identified herein as pho1-13, pho3-21, pho2-15, pho3-18, pho3-22, pho3-3, pho3-17, pho2-2, pho1-5, pho3-1, pho3-23, pho3-50, pho1-14, pho2-10, pho3-14, pho3-24 and pho3-29, obtainable from Group B Streptococcus, or a homologue or functional fragment thereof. Such a peptide is suitable for therapeutic use e.g. when isolated.

The term "functional fragments" is used herein to define a part of the gene or peptide which retains the activity of the whole gene or peptide. For example, a functional fragment of the peptide may be used as an antigenic determinant, useful in a vaccine or in the production of antibodies.

A gene fragment may be used to encode the active peptide. Alternatively, the gene fragment may have utility in gene therapy, targetting the wild-type gene in vivo to exert a therapeutic effect.

A peptide according to the present invention may comprise any of the amino acid sequences identified herein as SEQ ID NOS. 2, 4, 6, 8, 10, 11, 13, 15, 17, 19, 21, 23, 25, 27, 29, 31, 33 and 35, or a functional fragment thereof.

Because of the extracellular or cell surface location, the peptides of the present invention may be suitable candidates for the production of therapeutically-effective vaccines against GBS. The term "therapeutically-effective" is intended to include the prophylactic effect of vaccines. For example, a vaccine may comprise a peptide according to the invention, or the means for its expression, for th treatment of infection. The vaccine may be administered to females prior to or during pregnancy to protect mother and neonate against infection by GBS.

According to another aspect of the invention, the peptides or genes may be used for screening potential antimicrobial drugs or for the detection of virulence.

A further aspect of this invention is the use of any of the products identified herein, for the treatment or prevention of a condition associated with infection by a Group B Streptococcal strain.

Although the protein has been described for use in the treatment of patients, veterinary uses of the products of the invention are also considered to be within the scope of the present invention. In particular, the peptides or the vaccines may be used in the treatment of chronic mastitis, especially in cows.

DESCRIPTION OF THE INVENTION

The present invention is described with reference to Group B Streptococcal strain M732. However, all the GBS strains and many other bacterial strains are likely to include related peptides or proteins having amino acid sequence homology with the peptide of M732. Organisms likely to contain the peptides include, but are not limited to, *S. pneumoniae, S. pyogenes, S. suis, S. milleri*, Group C and Group G Streptococci and Enterococci. Vaccines to each of these may be developed in the same way as described for CBS.

Preferably, the peptides that may be useful for the production of vaccines have greater than 40% sequence similarity with the peptides identified herein. More preferably, the peptides have greater than 60% sequence similarity. Most preferably, the peptides have greater than 80% sequence similarity, e.g. 95% similarity.

Having characterised a gene according to the invention, it is possible to use the gene sequence to establish homologies in other microorganisms. In this way it is possible to determine whether other microorganisms have similar outer surface products. Sequence homologies may be established by searching in existing databases, e.g. EMBL or Genbank.

Peptides or proteins according to the invention may be purified and isolated by methods known in the art. In particular, having identified the gene sequence, it will be possible to use recombinant techniques to express the genes in a suitable host. Active fragments and homologues can be identified and may be useful in therapy. For example, the peptides or their active fragments may be used as antigenic determinants in a vaccine, to elicit an immune response. They may also be used in the preparation of antibodies, for passive immunisation, or diagnostic applications. Suitable antibodies include monoclonal antibodies, or fragments thereof, including single chain fv fragments. Methods for the preparation of antibodies will be apparent to those skilled in the art.

The preparation of vaccines based on attenuated microorganisms is known to those skilled in the art. Vaccine compositions can be formulated with suitable carriers or adjuvants, e.g. alum, as necessary or desired, and used in therapy, to provide effective immunisation against Group B Streptococci or other related microorganisms. The preparation of vaccine formulations will be apparent to the skilled person.

More generally, and as is well known to those skilled in the art, a suitable amount of an active component of the invention can be selected, for therapeutic use, as can suitable carriers or excipients, and routes of administration. These factors will be chosen or determined according to known criteria such as the nature/severity of the condition to be treated, the type or health of the subject etc.

The products of the present invention were identified as follows:

A partial gene library of GBS (strain M732) chromosomal DNA was prepared using the plasmid vectors pFW-phoA1, pFW-phoA2 and pFW-phoA3 (Podbielski, A. et al. 1996. Gene 177:137–147). These plasmids possess a constitutive spectinomycin adenyltransferase antibiotic resistance marker, which confers a high level of spectinomycin resistance and is therefore easily selected. Furthermore, these vectors contain a truncated (leaderless) *Escherichia coli* phoA gene for alkaline phosphatase. The three vectors differ only with respect to the reading frame in which the leaderless phoA gene exists, as compared to an upstream in-frame BamHI restriction enzyme site. Because this truncated *E. coli* phoA gene lacks the appropriate leader sequence for export of this enzyme across the bacterial membrane, extracellular alkaline phosphatase activity is absent when these plasmids are propagated in an *E. coli* phoA mutant (e.g. strain DH5α). The chromogenic alkaline phosphatase substrate, XP (5-bromo-4-chloro-3-indolyl-phosphate), does not enter intact bacterial cells and therefore only exported or surface associated alkaline phosphatase activity can be detected. When exported or surface associated alkaline phosphatase activity is present, the chromogenic XP substrate is cleaved to yield a blue pigment and the corresponding bacterial colonies can be identified by their blue colour.

Plasmid DNA was digested to completion with BamHI and dephosphorylated using shrimp alkaline phosphatase. GBS genomic DNA was partially digested with Sau3AI, siz fractionated on a sucrose gradient and fragments <1 kb in size were ligated into the prepared pFW-phoA vectors. *E. coli* strain DH5α was chosen as the cloning host since it lacks a functional phoA gene. Recombinant plasmids were selected on Luria agar containing 100 µg/ml of spectinomycin and 40 µg/ml of the chromogenic XP substrate. *E. coli* transformants harbouring plasmids containing GBS insert DNA that complements the export signal sequence of the leaderless phoA gene were identified by the blue colour of the colonies. Approximately 30000 different recombinant plasmids containing GBS insert DNA were screened in this manner and 83 recombinant plasmids, which complemented the leaderless phoA, were chosen for further study.

From these experiments, several clones were selected each containing a plasmid containing a gene (or part thereof), which complemented the leaderless phoA.

Having identified the gene in each clone it is then possible to obtain the full-length gene sequence, as follows.

Using the identified and sequenced gene fragment, oligonucleotide primers were designed for genomic DNA sequencing. These primers were designed so as to sequence in an 'outward' direction from the obtained sequence. Once read, the sequence obtained was checked to see if the 5' and 3' termini of the gene had been reached. The presence of these features was identified by checking against homologous sequences, and for the 5' end the presence of an AUG start codon (or accepted equivalent) preceded by a Shine-Dalgarno consensus sequence, and for the 3' end, the presence of a translation termination (Stop) codon.

Upon identification of the full-length gene, primers were designed for amplification of full-length product. Primers used included restriction enzyme recognition sites (NcoI at the 5'end and Eco0109I at the 3' end) to allow subsequent cloning of the product into the Lactococcal expression system used.

PCR was carried out using the primers, and the products cloned into a pCR 2.1 cloning vector (In Vitrogen). Following confirmation of the presence of the cloned fragment, the DNA was excised using the restriction enzymes NcoI and Eco0109I.

The vector into which this fragment was inserted was a modified version of pNZ8048 (Kuipers, O. P. et al. (1998) J. Biotech 64: 15–21). This vector, harbouring a lactococcal origin of replication, a chloramphenicol resistance marker, an inducible nisin promoter and a multicloning site was altered by the replacement of the multicloning site with two 10×His tags, flanked on the 5-most end with an NcoI site, split in the middle with a multicloning site (including an Eco0109I site), and a Stop (termination) codon at the 3'end of the His tags.

The gene of interest was inserted so that a 10×His tag was in the 3' position relative to the coding region. Following transformation of the recombinant plasmid into *L. lactis* (strain NZ9000—Kuipers, O. P. et al. (1998) *supra*), a 400 ml liquid culture was set up and translation of the protein was induced by the addition of nisin to the culture. After a 2 hour incubation, the cells were harvested and lysed by bead beating. The resultant lysate was cleared by centrifugation, then passed over a metal affinity (Talon, Clonetech) column. The column was washed repeatedly before bound proteins were eluted with Imidazole.

To identify fractions containing the His-tagged recombinant protein, an aliquot from each fraction was analysed by SDS-PAGE, Western blotted and probed with anti-His antibodies.

The recombinant protein obtained was then used to immunise New Zealand white rabbits, with pre-immune sera being harvested prior to immunisation. Following a boost, the rabbits were sacrificed and sera collected. This sera was used in Western blots, ELISA and animal protection models.

Using the sera obtained from the animal studies, immunosorption studies were carried out.

Group B Streptococcus was grown in 20 ml Todd Hewitt broth (THB) for 8 hours, harvested and resuspended in 5 ml PBS. 50 µl aliquots of this were used to coat wells in a 96 well plate (Nunc Immuno-Sorb). This was left at 4° C. overnight to allow for adsorbance of the bacteria onto the plate. Plates were washed twice with PBS, then blocked with 3% BSA in PBS for 1 hr at 37° C. Plates were again washed. Serial 10 fold dilutions of the sera were made in PBS and 50 µl of these dilutions were added to the wells of the plate, in duplicate. The plate was covered and incubated for 1 hr at 37° C. The plate was washed, then 50µl anti-rabbit alkaline phosphatase conjugated secondary antibody at a concentration of 1:5000 was added to each well. Following incubation at 37° C. for an hour, the plate was washed again. 50 µl substrate (PNPP) was added to each well, and the reaction allowed to proceed for 30 min before the adsorbance was read at 405 nm.

Animal protection studies were also carried out to test the effectiveness of protection on the immunised rabbits.

GBS M732 was grown up in THB until mid-log phase was reached—approximately 5 hours. Cells were counted in a counting chamber, and bacteria were diluted to give a concentration of 2×10$^7$ bacteria per ml in pre-immune or test sera. 50 µl of this was injected via the intraperitoneal route into 0–1 day old mice. The mice were observed for survival over 48 hours.

The following Examples illustrate the invention.

EXAMPLE 1

A first clone contained a gene sequence identified herein as SEQ ID NO. 1, with an amino acid sequence identified as SEQ ID NO. 2, and classified as pho1-13.

A comparison of the amino acid sequence of pho1-13 was performed.

Homologues to the GBS pho1-13 gene product can be identified in *Streptococcus pyogenes, S. pneumoniae, S. salivarius, Escherichia coli, Yersinia enterocolitica, Aquifex aeolicus, Helicobacter pylon* and *Haemophilus influenzae*. The *S. pyogenes* and *S. pneumoniae* homologues were identified from genome sequence data and no annotations were available as to the identity of the gene or gene products. In all other cases, the above homologues can be identified as ATP-dependent Clp protease proteolytic subunits. The catalytic activity of Clp proteases results in the hydrolysis of proteins to small peptides in the presence of ATP and magnesium (Giffard, P. M. et al. 1993. J. Gen. Microbiol. 139:913–920). Furthermore, the ClpP component of Clp proteases has been shown to be induced as part of the heat shock response (Kroh, H. E. and L. D. Simon. 1990. J. Bacteriol. 172:6026–6034) and it is probable that this subunit or the complete proteolytic domain would associated with the bacterial surface.

Immunisation studies, carried out as described above, yielded the following results.

| Treatment | No animals | No animals surviving at time (hrs) | |
|---|---|---|---|
| | | 24 | 48 |
| PBS | 10 | 7 | 0 |
| Pre-immunised | 37 | 13 | 0 |
| Immunised | 38 | 17 | 9 |

EXAMPLE 2

A second clone was selected containing a plasmid designated pho1-14. This plasmid contained a gene (or part thereof), which complemented the leaderless phoA. The nucleotide and deduced amino acid sequences are shown as SEQ ID NOS. 3 and 4, respectively.

A comparison of the amino acid sequence of pho1-14 was performed.

Homologues to the GBS pho1-14 gene product can be identified in *Streptococcus pyogenes, Enterococcus faecalis* and *Streptococcus pneumoniae*. These homologues were identified from genome sequence data and no annotations were available as to the identity of the gene or gene products. Additionally, two possible homologues were also identified from *Shigella flexneri* (SpaR) and *Yersinia pseudotuberculosis* (YscT). These latter two homologues are related proteins, believed to be anchored in the bacterial membrane (Bergman, T. et al. 1994. J. Bacteriol. 176:2619–2626). In *S. flexneri*, the product of the spaR gene has been shown to be important for invasion of epithelial cells (Sasakawa, C. et al. 1993. J. Bacteriol. 175:2334–2346). Furthermore, the product of the spaR gene is also required for surface presentation of invasion plasmid antigens. The analogous protein in *Y. pseudotuberculosis* is a component of the Yop secretion system and is also important for virulence in this organism.

EXAMPLE 3

A third clone was selected containing a plasmid designated pho1-5. This plasmid contained a gene (or part thereof), which complemented the leaderless phoA. Th nucleotide and deduced amino acid sequences are shown as SEQ ID NOS. 5 and 6.

A comparison of the amino acid sequence of pho1-5 was performed.

Homologues to the GBS pho1-5 gene product can only be identified in *Streptococcus pyogenes* and *Staphylococcus carnosus* (sceA). The *S. pyogenes* homologue was identified from genome sequence data and no annotations were available as to the identity of the gene or gene products. Furthermore, little information is available on the function of the sceA gene product from *S. carnosus*. The sceA gene product shows some sequence similarity to the aggregation promoting protein from *Lactobacillus gasseri*. Based on analysis of the sceA gene product, this molecule contains a well-conserved signal sequence and is apparently secreted or associated with the bacterial cell surface.

EXAMPLE 4

A further clone was selected containing a plasmid designated pho3-3. This plasmid contained a gene (or part thereof), which complemented the leaderless phoA. The nucleotide and deduced amino acid sequences are shown as SEQ ID NOS. 7 and 8.

A comparison of the amino acid sequence of pho3-3 was performed.

Homologues to the GBS pho3-3 gene product can be identified in *Streptococcus mutans* (rmiC), (cpsM) *S. pneumoniae* and *S. pyogenes*. The *S. pyogenes* homologue was identified from genome sequence data and no annotations were available as to the identity of the gene or gene product. In *S. pneumoniae*, the homologue can be identified as dTDP-4-keto-6-deoxy glucose-3,5-epimerase. In the other two cases, the above homologues can be identified as dTDP-4-keto-L-rhamnose reductase (rmlC). In *S. mutants*, the gene encoding this enzyme, rmlC, is part of the rml locus. The rml locus consists of three genes which exhibit significant similarity to enzymes involved in the biosynthesis of dTDP-rhamnose, the immediate precursor of the rhamnose component in the *S. mutans* polysaccharide capsule (Tsukioka, Y. et al. 1997. J. Bacteriol. 179:1126–1134). An analogous locus has also been identified in *S. pneumoniae* (Coffey, T. J. et al. 1998. Mol. Micobiol. 17:73–83). Almost all Streptococci characteristically possess rhamnose in their cell wall associated polysaccharides (Schleifer, K. H. and R. Kilper-Bälz. 1987. Syst. Appl. Microbiol. 10:1–19), and it is highly probable that dTDP-4-keto-L-rhamnose reductase would be associated with the outer surface in Streptococci.

EXAMPLE 5

A further clone was selected containing a plasmid designated pho2-10. This plasmid contained a gene (or part thereof), which complemented the leaderless phoA.

The nucleotide sequence is shown as SEQ ID NO. 9. From this, upstream and downstream coding regions were identified, and the deduced amino acid sequences shown as SEQ ID NOS. 10 and 11.

A comparison of the amino acid sequences of pho2-10 was performed.

Homologues to the CBS pho2-10 gene product can be identified in *Streptococcus pyogenes, Enterococcus faecalis, Debaryomyces occidentalis* (hatI) and *Escherichia coli* (trkD). The *S. pyogenes* and *E. faecalis* homologues were identified from genome sequence data and no annotations were available as to the identity of the gene or gene products. In the yeast *D. occidentalis*, the hak1 gene is a homologue of the trkD gene from *E. coli* (Banuelos, M. A. et al. 1995. EMBO J. 14:3021–3027). The trkD gene of *E. coli* is part of the kup potassium uptake system. The specific homolog identified here is the kup system potassium uptake protein. The kup system is a constitutive potassium uptake system in *E. coli*. The kup system potassium uptake protein contains a highly hydrophobic N-terminus that is predicted to span the membrane at least 12 times. Kup is not homologous to other known membrane protein sequences. There is no indication of ATP binding, and it is proposed that the system is driven by a chemiosmotic gradient (Schleyer, M. & E. P. Bakker, 1993. J. Bacteriol. 175:6925–6931).

EXAMPLE 6

A further clone was selected containing a plasmid designated pho2-15. This plasmid contained a gene (or part thereof), which complemented the leaderless phoA. The nucleotide and deduced amino acid sequences of the gene are shown as SEQ ID NOS. 12 and 13.

A comparison of the amino acid sequence of pho2-15 was performed.

Homologues to the CBS pho2-15 gene product can be identified in *Streptococcus pyogenes, Streptococcus pneumoniae, Enterococcus faecalis* and *Escherichia coli* (gatc and SgcC). The *S. pyogenes, S. pneumoniae* and *E. faecalis* homologues were identified from genome sequence data and no annotations were available as to the identity of the gene or gene products. In *E. coli*, the gatC and sgcC gene products can be identified as being the IIC component of phosphoenolypyruvate-dependent sugar phosphotransferase systems (PTS), a major carbohydrate active-transport system. In PTS systems, the IIC component is typically involved in binding of extracellular carbohydrates and forms a complex with the IID component to constitute a membrane channel (Nobelmann, B. and J. W. Lengeler. 1995. Biochim. Biophys. Acta 1262:69–72).

EXAMPLE 7

A further clone was selected containing a plasmid designated pho2-2. This plasmid contained a gene (or part thereof), which complemented the leaderless phoA. The nucleotide and deduced amino acid sequences of the gene are shown as SEQ ID NOS. 14 and 15, respectively.

A comparison of the amino acid sequence of pho2-2 was performed.

Homologues to the GBS pho2-2 gene product can be identified in *Enterococcus faecalis, Escherichia coli* (malK and afuC), *Bacillus subtilis* (glnO), *Haemophilus influenzae* (yebM and potA), *Streptococcus pyogenes, Streptococcus pneumoniae* and *Salmonella typhimurium* (malK). The *E. faecalis, S. pyogenes* and *S. pneumoniae* homologues were identified from genome sequence data and no annotations were available as to the identity of the gene or gene products. In all other cases, homologues represented ATP-binding transport proteins that are part of ABC type transporters. Many of the components of ABC type transporters are membrane or cell surface associated, as these systems are involved in the transport of macromolecules from the extracellular environment to the intracellular compartment.

EXAMPLE 8

A further clone was selected containing a plasmid designated pho3-14. This plasmid contained a gene (or part thereof), which complemented the leaderless phoA. The nucleotide and deduced amino acid sequences of the gene are shown as SEQ ID NOS. 16 and 17.

A comparison of the amino acid sequence of pho3-14 was performed and no homologues could be identified in any of the public databases. One homologue to the CBS pho3-14 gene product can be identified in *Streptococcus pyogenes*, but this homologue was identified from genome sequence data and no annotations were available as to the identity of th gene or gene product. Using this *S. pyogenes* homologue to search the public databases yielded no further information. Since the pho3-14 product complemented the leaderless phoA gene, it can be concluded that this protein (or part thereof) would most probably be located extracellularly.

EXAMPLE 9

A further clone was selected containing a plasmid designated pho3-17. This plasmid contained a gene (or part thereof), which complemented the leaderless phoA. The nucleotide and deduced amino acid sequences of the gene are shown as SEQ ID NOS. 18 and 19.

A comparison of the amino acid sequence of pho3-17 was performed.

Homologues to the GBS Pho3-17 gene product can be identified in *Streptococcus mutans* and *Lactococcus lactis*, with similarity being shown to N-acetyl muramidase. Similarity is also seen with an unidentified gene, yubE from *Bacillus subtilis*.

N-acetylmuramidase is an autolysin that is involved in cell division. Using this limited information along with the fact that pho3-17 complemented the leaderless phoA gene, it can be concluded that the pho3-17 product would most probably be located extracellularly.

EXAMPLE 10

A further clone was selected containing a plasmid designated pho3-18. This plasmid contained a gene (or part thereof), which complemented the leaderless phoA. The nucleotide and deduced amino acid sequences of the gene are shown as SEQ ID NOS. 20 and 21.

A comparison of the amino acid sequence of pho3-18 was performed.

Homologues to the CBS pho3-18 gene product can be identified in *Streptococcus pyogenes* and *Streptococcus pneumoniae*. These homologues were identified from genome sequence data and no annotations were available as to the identity of the gene or gene products. Using these *S. pyogenes* and *S. pneumoniae* homologues to search the public databases showed some similarity to outer surface and membrane spanning proteins. Since the ORF3-18 product complemented the leaderless phoA gene, it can be concluded that this protein (or part thereof) would most probably be located extracellularly.

EXAMPLE 11

A further clone was selected containing a plasmid designated pho3-1. This plasmid contained a gene (or part thereof), which complemented the leaderless phoA. The nucleotide and deduced amino acid sequences of the gene are shown as SEQ ID NOS. 22 and 23.

A comparison of the amino acid sequence of pho3-1 was performed.

Homologues to the GBS pho3-1 gene product can be identified in *Streptococcus pyogenes, Streptococcus pneumoniae, Bacillus subtilis* (yutD) and *Enterococcus faecalis*. The *S. pyogenes, S. pneumoniae* and *E. faecalis* homologues were identified from genome sequence data and no annotations were available as to the identity of the gene or gene products. In *B. subtilis*, the function of the yutD gene product is unknown. It can be noted however, that the yutD gene is located on the *B. subtilis* chromosome in a region containing genes involved in cell wall synthesis. The fact that this DNA sequence complemented the leaderless phoA gene suggests that this gene product is extracellularly located.

EXAMPLE 12

A further clone was selected containing a plasmid designated pho3-21. This plasmid contained a gene (or part thereof), which complemented the leaderless phoA. The nucleotide and deduced amino acid sequences of the gene are shown as SEQ ID NOS. 24 and 25.

A comparison of the amino acid sequence of pho3-21 was performed.

Homologues to the GBS pho3-21 gene product can be identified in *Streptococcus pyogenes, Streptococcus pneumoniae, Lactobacillus fermentum* (bspA) and *Lactobacillus reuteri* (cnb). The *S. pyogenes* and *S. pneumoniae* homologues were identified from genome sequence data and no annotations were available as to the identity of the gene or gene products. In *L. fermentum*, the bspA gene product has been identified as being a basic cell surface-located protein that has some sequence similarity to family III of the bacterial solute-binding proteins (Turner, M. S. et al. 1997. J. Bacteriol. 179:3310–3316). In *L. reuteri*, the cnb gene product has been identified as a collagen binding protein that has some sequence similarity to the solute-binding component of bacterial ABC transporters (Roos, S. et al. 1996. FEMS Microbiol. Lett. 144:33–38).

EXAMPLE 13

A further clone was selected containing a plasmid designated pho3-22. This plasmid contained a gene (or part thereof), which complemented the leaderless phoA. The nucleotide and deduced amino acid sequences of the gene are shown as SEQ ID NOS. 26 and 27.

A comparison of the amino acid sequence of pho3-22 was performed.

Homologues to the GBS pho3-22 gene product can be identified in *Enterococcus faecalis, Streptococcus equisimilis* (lppC), *Pseudomonas fluorescens* (oprI) and *Streptococcus thermophilus* (orf142). The *E. faecalis* homolog was identified from genome sequence data and no annotations were available as to the identity of the gene or gene products. In *S. equisimilis*, the lppC gene product has been identified as being a lipoprotein that is homologous to the E(P4) outer membrane protein from *Haemophilus influenzae* (Gase, K. et al. 1997. Med. Microbiol. Immunol. 186:63–73). Likewise, the P. fluorescens oprI gene encodes a major outer membrane lipoprotein (Cornelis, P. et al. 1989. Mol. Microbiol. 3:421–428). In *S. thermophilus*, the orf142 product has been putatively identified as a cell surface exposed lipoprotein that may act as a receptor for the bacteriophages TP-J34 and Sfi21 (Neve, H. et al. 1998. Virology 241:61–72). The ORF3-22 product showed good similarity to the above homologues, particularly at the N-terminus. This is most likely the region required for complementation of the leaderless phoA gene, and therefore serves as a leader sequence.

EXAMPLE 14

A further clone was selected containing a plasmid designated pho3-23. This plasmid contained a gene (or part thereof), which complemented the leaderless phoA. The nucleotide and deduced amino acid sequences of the genes are shown as SEQ ID NOS. 28 and 29.

A comparison of the amino acid sequence of pho3-23 was performed.

Homologues to the GBS pho3-23 gene product can be identified in *Streptococcus pyogenes, Streptococcus pneumoniae, Enterococcus faecalis* and *Streptococcus mutans* (perM). The *S. pyogenes, S. pneumoniae* and *E. faecalis* homologues were identified from genome sequence data and no annotations were available as to the identity of the gene or gene products. In *S. mutans*, the perM gene product has been presumptively identified as a permease, but no other information is available as to the function of this protein. Considering that the pho3-23 coding region complements the leaderless phoA gene, it can be concluded that the pho3-17 gene product would most probably be located extracellularly.

EXAMPLE 15

A further clone was selected containing a plasmid designated pho3-24. This plasmid contained a gene (or part thereof), which complemented the leaderless phoA. The nucleotide and deduced amino acid sequences of the gene are shown as SEQ ID NOS. 30 and 31.

A comparison of the amino acid sequence of pho3-24 was performed.

Homologues to the GBS pho3-24 gene product can be identified in *Streptococcus mutans* (dltB), *Streptococcus pneumoniae, Streptococcus pyogenes, Enterococcus faecalis, Lactobacillus casei* (dltB) and *Bacillus subtilis* (dltB). The *S. pneumoniae, S. pyogenes* and *E. faecalis* homologues were identified from genome sequence data and no annotations were available as to the identity of the gene or gene products. In *S. mutans, L. casei* and *B. subtilis*, the dltB gene product has been identified as being a basic membrane protein that is involved in the transport of activated D-alanine through the cell membrane. The dltB gene product is involved in the biosynthesis of D-alanyl-lipoteichoic acid (Heaton, M. P. and F. C. Neuhaus. 1992. J. Bacteriol. 174:4707–4717). In *L. casei* and *B. subtilis*, the dltB gene product is believed to contain at least 9 membrane spanning domains, indicating that the protein or portions thereof are exposed to the outside of the cell.

EXAMPLE 16

A further clone was selected containing a plasmid designated pho3-29. This plasmid contained a gene (or part thereof), which complemented the leaderless phoA. The nucleotide and deduced amino acid sequences of the gene are shown as SEQ ID NOS. 32 and 33.

A comparison of the amino acid sequence of pho3-29 was performed.

Homologues to the GBS pho3-29 gene product can be identified in *Borrelia burgdorferi* (p23 or ospC), *Bacillus brevis* (owp) and *Pseudomonas aeruginosa* (oprI). Although these homologues are not related to each other, they all represent major outer surface proteins. In *B. burgdorferi*, the ospC gene product has been identified as being a 23-kDa protein that is the immunodominant antigen on the surface of this bacterium (Padula, S. J. et al. 1993. Infect. Immun. 61:5097–5105). The owp gene product from *B. brevis* is one of two major cell wall proteins involved in the surface layer lattice (Tsuboi, A. 1988. J. Bacteriol. 170:935–945). Finally, the oprI gene from *P. aeruginosa* encodes a major outer membrane lipoprotein precursor (Saint-Onge, A. et al. 1992. J. Gen. Microbiol. 138:733–741).

EXAMPLE 17

A further clone was selected containing a plasmid designated pho3-50. This plasmid contained a gene (or part thereof), which complemented the leaderless phoA. The nucleotide and deduced amino acid sequences of the gene are shown as SEQ ID NOS. 34 and 35.

A comparison of the amino acid sequence of pho3-50 was performed.

Homologues to the GBS pho3-50 gene product can be identified in a variety of Streptococci (penA, pbp2B, pbpB2), *Borrelia burgdorferi* (pbp2), *Enterococcus faecalis* (pbpC), *Staphylococcus aureus* (pbpA), *Mycobacterium leprae* (pbpB) and *Helicobacter pylori* (pbp2). In all cases, the above homologues can be identified as penicillin binding proteins (PBPs). Genes encoding penicillin binding proteins are often located in a cluster of genes associated with cell wall synthesis (Pucci, M. J. et al. 1997. J. Bacteriol. 179:5632–5635). Furthermore, PBPS are typically integrated into the cell wall of a bacterium with some or all of the protein being exposed on the outer bacterial surface.

What is claimed is:

1. A method for the treatment of a condition associated with Group B Streptococcal infection caused by *Streptococcus agalactiae*, wherein said method comprises administering to a patient an effective amount of an isolated peptide comprising the amino acid sequence of SEQ ID NO:23, or an isolated peptide comprising the immunogenic portion of SEQ ID NO:23, wherein said immunogenic portion induces an immune response and selectively binds to anti-*Streptococcus agalactiae* antibody specific for SEQ ID NO: 23.

2. The method according to claim 1, wherein said peptide comprising the amino acid sequence of SEQ ID NO:23 is administered to the patient.

3. The method according to claim 1, wherein the infection is a local infection.

4. The method according to claim 1, wherein the infection is a urinary tract infection.

5. A method for the prevention of a condition associated with Group B Streptococcal infection caused by *Streptococcus agalactiae*, wherein said method comprises administering to a patient an effective amount of an isolated peptide comprising the amino acid sequence of SEQ ID NO:23, or an isolated peptide comprising the immunogenic portion of SEQ ID NO: 23, wherein said immunogenic portion induces an immune response and selectively binds to anti-*Streptococcus agalactiae* antibody specific for SEQ ID NO: 23.

6. The method according to claim 5, wherein said peptide comprises comprising the amino acid sequence of SEQ ID NO:23 is administered to the patient.

7. The method according to claim 5, wherein the infection is a local infection.

8. The method according to claim 5, wherein the infection is a urinary tract infection.

* * * * *

UNITED STATES PATENT AND TRADEMARK OFFICE
CERTIFICATE OF CORRECTION

PATENT NO. : 6,812,021 B1
DATED : November 2, 2004
INVENTOR(S) : Martin John Glenton Hughes et al.

It is certified that error appears in the above-identified patent and that said Letters Patent is hereby corrected as shown below:

<u>Column 63,</u>
Lines 6-7, "peptide comprises comprising the" should read -- peptide comprising the --.

Signed and Sealed this

Fifth Day of April, 2005

JON W. DUDAS
*Director of the United States Patent and Trademark Office*

SEQUENCE LISTING

```
<160> NUMBER OF SEQ ID NOS: 35

<210> SEQ ID NO 1
<211> LENGTH: 587
<212> TYPE: DNA
<213> ORGANISM: Streptococcus agalactiae
<220> FEATURE:
<221> NAME/KEY: CDS
<222> LOCATION: (1)..(582)
<223> OTHER INFORMATION:
```

<400> SEQUENCE: 1

```
atg atc cca gta gta atc gaa caa aca agt cgt ggt gaa cgt tct tat     48
Met Ile Pro Val Val Ile Glu Gln Thr Ser Arg Gly Glu Arg Ser Tyr
1               5                   10                  15 gat att tac tca cgt ctt tta aaa gat cgt att att atg ttg aca ggc     96
Asp Ile Tyr Ser Arg Leu Leu Lys Asp Arg Ile Ile Met Leu Thr Gly
            20                  25                  30 caa gtt gag gat aat atg gcc aat agt atc att gca cag tta ttg ttt    144
Gln Val Glu Asp Asn Met Ala Asn Ser Ile Ile Ala Gln Leu Leu Phe
        35                  40                  45 ctc gat gca caa gat aat aca aag gat att tac ctt tat gtc aat aca    192
Leu Asp Ala Gln Asp Asn Thr Lys Asp Ile Tyr Leu Tyr Val Asn Thr
50                  55                  60 cca ggt ggt tca gta tcg gct gga ctt gct att gtg gac acc atg aac    240
Pro Gly Gly Ser Val Ser Ala Gly Leu Ala Ile Val Asp Thr Met Asn
65                  70                  75                  80 ttc att aaa tcg gac gta cag acg att gtt atg ggg atg gct gct tcg    288
Phe Ile Lys Ser Asp Val Gln Thr Ile Val Met Gly Met Ala Ala Ser
                85                  90                  95 atg gga acc att att gct tca agt ggt gct aaa gga aaa cgt ttt atg    336
Met Gly Thr Ile Ile Ala Ser Ser Gly Ala Lys Gly Lys Arg Phe Met
            100                 105                 110 tta ccg aat gca gaa tat atg atc cac caa cca atg ggc gga aca ggc    384
Leu Pro Asn Ala Glu Tyr Met Ile His Gln Pro Met Gly Gly Thr Gly
        115                 120                 125 gga ggt aca cag caa tct gat atg gct atc gct gct gag cat ctt tta    432
Gly Gly Thr Gln Gln Ser Asp Met Ala Ile Ala Ala Glu His Leu Leu
130                 135                 140 aaa acg cgt cat act tta gaa aaa atc tta gct gat aat tct ggt caa    480
Lys Thr Arg His Thr Leu Glu Lys Ile Leu Ala Asp Asn Ser Gly Gln
145                 150                 155                 160 tct att gaa aaa gtc cat gat gat gca gag cgt gat cgt tgg atg agt    528
Ser Ile Glu Lys Val His Asp Asp Ala Glu Arg Asp Arg Trp Met Ser
                165                 170                 175 gct caa gaa aca ctt gat tat ggc ttt att gat gaa atc atg gct aat    576
Ala Gln Glu Thr Leu Asp Tyr Gly Phe Ile Asp Glu Ile Met Ala Asn
            180                 185                 190 aat gaa taagg                                                       587
Asn Glu
```

<210> SEQ ID NO 2
<211> LENGTH: 194
<212> TYPE: PRT
<213> ORGANISM: Streptococcus agalactiae

<400> SEQUENCE: 2

```
Met Ile Pro Val Val Ile Glu Gln Thr Ser Arg Gly Glu Arg Ser Tyr
1               5                   10                  15

Asp Ile Tyr Ser Arg Leu Leu Lys Asp Arg Ile Ile Met Leu Thr Gly
            20                  25                  30

Gln Val Glu Asp Asn Met Ala Asn Ser Ile Ile Ala Gln Leu Leu Phe
        35                  40                  45

Leu Asp Ala Gln Asp Asn Thr Lys Asp Ile Tyr Leu Tyr Val Asn Thr
50                  55                  60

Pro Gly Gly Ser Val Ser Ala Gly Leu Ala Ile Val Asp Thr Met Asn
65                  70                  75                  80

Phe Ile Lys Ser Asp Val Gln Thr Ile Val Met Gly Met Ala Ala Ser
                85                  90                  95
```

```
Met Gly Thr Ile Ile Ala Ser Ser Gly Ala Lys Gly Lys Arg Phe Met
            100                 105                 110
Leu Pro Asn Ala Glu Tyr Met Ile His Gln Pro Met Gly Gly Thr Gly
        115                 120                 125
Gly Gly Thr Gln Gln Ser Asp Met Ala Ile Ala Ala Glu His Leu Leu
        130                 135                 140
Lys Thr Arg His Thr Leu Glu Lys Ile Leu Ala Asp Asn Ser Gly Gln
145                 150                 155                 160
Ser Ile Glu Lys Val His Asp Asp Ala Glu Arg Asp Arg Trp Met Ser
                165                 170                 175
Ala Gln Glu Thr Leu Asp Tyr Gly Phe Ile Asp Glu Ile Met Ala Asn
            180                 185                 190
Asn Glu
```

<210> SEQ ID NO 3
<211> LENGTH: 218
<212> TYPE: DNA
<213> ORGANISM: Streptococcus agalactiae
<220> FEATURE:
<221> NAME/KEY: CDS
<222> LOCATION: (1)..(216)
<223> OTHER INFORMATION:

<400> SEQUENCE: 3

```
atc aga gca tat tct ggt cct ctt tcg gtt ttc ctg cca cgt ttt aaa        48
Ile Arg Ala Tyr Ser Gly Pro Leu Ser Val Phe Leu Pro Arg Phe Lys
1               5                   10                  15 gct tgt gat ata ata gtc aat gtg agg agg act atc atg tta ttt aag        96
Ala Cys Asp Ile Ile Val Asn Val Arg Arg Thr Ile Met Leu Phe Lys
            20                  25                  30 gaa aaa att cct gga cta ata tta tgc ttt att att gct ata cca tct       144
Glu Lys Ile Pro Gly Leu Ile Leu Cys Phe Ile Ile Ala Ile Pro Ser
        35                  40                  45 tgg ttg ctt ggg ctt tat ctc cct tta ata gga gca cca gtc ttt gct       192
Trp Leu Leu Gly Leu Tyr Leu Pro Leu Ile Gly Ala Pro Val Phe Ala
    50                  55                  60 atc ttg att gga ata att gtt gga tc                                    218
Ile Leu Ile Gly Ile Ile Val Gly
65                  70
```

<210> SEQ ID NO 4
<211> LENGTH: 72
<212> TYPE: PRT
<213> ORGANISM: Streptococcus agalactiae

<400> SEQUENCE: 4

```
Ile Arg Ala Tyr Ser Gly Pro Leu Ser Val Phe Leu Pro Arg Phe Lys
1               5                   10                  15

Ala Cys Asp Ile Ile Val Asn Val Arg Arg Thr Ile Met Leu Phe Lys
            20                  25                  30

Glu Lys Ile Pro Gly Leu Ile Leu Cys Phe Ile Ile Ala Ile Pro Ser
        35                  40                  45

Trp Leu Leu Gly Leu Tyr Leu Pro Leu Ile Gly Ala Pro Val Phe Ala
    50                  55                  60

Ile Leu Ile Gly Ile Ile Val Gly
65                  70
```

<210> SEQ ID NO 5
<211> LENGTH: 705
<212> TYPE: DNA
<213> ORGANISM: Streptococcus agalactiae
<220> FEATURE:
<221> NAME/KEY: CDS
<222> LOCATION: (1)..(705)
<223> OTHER INFORMATION:

<400> SEQUENCE: 5

| | | | | | | | | | | | | | | | | |
|---|---|---|---|---|---|---|---|---|---|---|---|---|---|---|---|---|
| atg | aat | aaa | aga | aga | aaa | tta | tca | aaa | ttg | aat | gta | aaa | aar | caa | cat | 48 |
| Met | Asn | Lys | Arg | Arg | Lys | Leu | Ser | Lys | Leu | Asn | Val | Lys | Lys | Gln | His | |
| 1 | | | | 5 | | | | | 10 | | | | | 15 | | |
| tta | gct | tat | gga | gct | atc | act | tta | gta | gcc | ctt | ttt | tca | tgt | att | ttg | 96 |
| Leu | Ala | Tyr | Gly | Ala | Ile | Thr | Leu | Val | Ala | Leu | Phe | Ser | Cys | Ile | Leu | |
| | | | | 20 | | | | | 25 | | | | | 30 | | |
| gct | gta | acg | gtc | atc | ttt | aaa | agt | tca | caa | gtt | act | act | gaa | tct | ttg | 144 |
| Ala | Val | Thr | Val | Ile | Phe | Lys | Ser | Ser | Gln | Val | Thr | Thr | Glu | Ser | Leu | |
| | | 35 | | | | | 40 | | | | | 45 | | | | |
| tca | aaa | gca | gat | aaa | gtt | cgc | gta | gcc | aaa | aaa | tca | aaa | atg | act | aag | 192 |
| Ser | Lys | Ala | Asp | Lys | Val | Arg | Val | Ala | Lys | Lys | Ser | Lys | Met | Thr | Lys | |
| | 50 | | | | | 55 | | | | | 60 | | | | | |
| gcg | aca | tct | aaa | tca | aaa | gta | gaa | gat | gta | aaa | cag | gct | cca | aaa | cct | 240 |
| Ala | Thr | Ser | Lys | Ser | Lys | Val | Glu | Asp | Val | Lys | Gln | Ala | Pro | Lys | Pro | |
| 65 | | | | | 70 | | | | | 75 | | | | | 80 | |
| tct | cag | gca | tct | aat | gaa | gcc | cca | aaa | tca | agt | tct | caa | tct | aca | gaa | 288 |
| Ser | Gln | Ala | Ser | Asn | Glu | Ala | Pro | Lys | Ser | Ser | Ser | Gln | Ser | Thr | Glu | |
| | | | | 85 | | | | | 90 | | | | | 95 | | |
| gct | aat | tct | cag | caa | caa | gtt | act | gcg | agt | gaa | gag | acg | gct | gta | gaa | 336 |
| Ala | Asn | Ser | Gln | Gln | Gln | Val | Thr | Ala | Ser | Glu | Glu | Thr | Ala | Val | Glu | |
| | | | 100 | | | | | 105 | | | | | 110 | | | |
| caa | gca | gtt | gta | aca | gaa | ata | ccc | ctg | cta | cca | gtc | agg | cac | aac | aac | 384 |
| Gln | Ala | Val | Val | Thr | Glu | Ile | Pro | Leu | Leu | Pro | Val | Arg | His | Asn | Asn | |
| | | 115 | | | | | 120 | | | | | 125 | | | | |
| ctt | tat | gct | gtt | act | gag | aca | cct | tac | aac | cct | gct | caa | cca | cca | gac | 432 |
| Leu | Tyr | Ala | Val | Thr | Glu | Thr | Pro | Tyr | Asn | Pro | Ala | Gln | Pro | Pro | Asp | |
| | 130 | | | | | 135 | | | | | 140 | | | | | |
| caa | gtg | gcc | agg | tat | gag | caa | tgg | aaa | tac | tgc | cag | gcg | gtc | gga | tct | 480 |
| Gln | Val | Ala | Arg | Tyr | Glu | Gln | Trp | Lys | Tyr | Cys | Gln | Ala | Val | Gly | Ser | |
| 145 | | | | | 150 | | | | | 155 | | | | | 160 | |
| gct | gct | gca | gca | caa | atg | gct | gct | gca | aca | gga | gtc | cct | cag | tct | act | 528 |
| Ala | Ala | Ala | Ala | Gln | Met | Ala | Ala | Ala | Thr | Gly | Val | Pro | Gln | Ser | Thr | |
| | | | | 165 | | | | | 170 | | | | | 175 | | |
| tgg | gaa | cat | att | att | gcc | cgt | gaa | tca | aat | ggt | aat | cct | aat | gtt | gct | 576 |
| Trp | Glu | His | Ile | Ile | Ala | Arg | Glu | Ser | Asn | Gly | Asn | Pro | Asn | Val | Ala | |
| | | | | 180 | | | | | 185 | | | | | 190 | | |
| aat | gcc | tca | gga | gct | tca | gga | ctt | ttc | caa | acg | atg | cca | ggt | tgg | ggt | 624 |
| Asn | Ala | Ser | Gly | Ala | Ser | Gly | Leu | Phe | Gln | Thr | Met | Pro | Gly | Trp | Gly | |
| | | | 195 | | | | | 200 | | | | | 205 | | | |
| tca | aca | gct | aca | gtt | cag | gat | caa | gta | att | cag | cta | tta | aag | ctt | att | 672 |
| Ser | Thr | Ala | Thr | Val | Gln | Asp | Gln | Val | Ile | Gln | Leu | Leu | Lys | Leu | Ile | |
| | 210 | | | | | 215 | | | | | 220 | | | | | |
| cgt | gct | caa | ggg | tta | tca | gct | ggg | tac | cag | tga | | | | | | 705 |
| Arg | Ala | Gln | Gly | Leu | Ser | Ala | Gly | Tyr | Gln | | | | | | | |
| 225 | | | | 230 | | | | | | | | | | | | |

<210> SEQ ID NO 6
<211> LENGTH: 234
<212> TYPE: PRT
<213> ORGANISM: Streptococcus agalactiae

<400> SEQUENCE: 6

| | | | | | | | | | | | | | | | |
|---|---|---|---|---|---|---|---|---|---|---|---|---|---|---|---|
| Met | Asn | Lys | Arg | Arg | Lys | Leu | Ser | Lys | Leu | Asn | Val | Lys | Lys | Gln | His |
| 1 | | | | 5 | | | | | 10 | | | | | 15 | |
| Leu | Ala | Tyr | Gly | Ala | Ile | Thr | Leu | Val | Ala | Leu | Phe | Ser | Cys | Ile | Leu |

-continued

```
                    20                  25                  30
Ala Val Thr Val Ile Phe Lys Ser Ser Gln Val Thr Thr Glu Ser Leu
                35                  40                  45

Ser Lys Ala Asp Lys Val Arg Val Ala Lys Lys Ser Lys Met Thr Lys
 50                  55                  60

Ala Thr Ser Lys Ser Lys Val Glu Asp Val Lys Gln Ala Pro Lys Pro
65                  70                  75                  80

Ser Gln Ala Ser Asn Glu Ala Pro Lys Ser Ser Gln Ser Thr Glu
                85                  90                  95

Ala Asn Ser Gln Gln Gln Val Thr Ala Ser Glu Glu Thr Ala Val Glu
                100                 105                 110

Gln Ala Val Val Thr Glu Ile Pro Leu Leu Pro Val Arg His Asn Asn
            115                 120                 125

Leu Tyr Ala Val Thr Glu Thr Pro Tyr Asn Pro Ala Gln Pro Pro Asp
    130                 135                 140

Gln Val Ala Arg Tyr Glu Gln Trp Lys Tyr Cys Gln Ala Val Gly Ser
145                 150                 155                 160

Ala Ala Ala Ala Gln Met Ala Ala Thr Gly Val Pro Gln Ser Thr
                165                 170                 175

Trp Glu His Ile Ile Ala Arg Glu Ser Asn Gly Asn Pro Asn Val Ala
                180                 185                 190

Asn Ala Ser Gly Ala Ser Gly Leu Phe Gln Thr Met Pro Gly Trp Gly
            195                 200                 205

Ser Thr Ala Thr Val Gln Asp Gln Val Ile Gln Leu Leu Lys Leu Ile
        210                 215                 220

Arg Ala Gln Gly Leu Ser Ala Gly Tyr Gln
225                 230
```

<210> SEQ ID NO 7
<211> LENGTH: 594
<212> TYPE: DNA
<213> ORGANISM: Streptococcus agalactiae
<220> FEATURE:
<221> NAME/KEY: CDS
<222> LOCATION: (1)..(594)
<223> OTHER INFORMATION:

<400> SEQUENCE: 7

```
atg act gaa cca ttt ttt gat aaa gaa tta act tgt cgc cca att gaa      48
Met Thr Glu Pro Phe Phe Asp Lys Glu Leu Thr Cys Arg Pro Ile Glu
1               5                   10                  15 gcc att cct gaa ttg ttg gaa ttc gat att acc gtt cgt gga gac aac      96
Ala Ile Pro Glu Leu Leu Glu Phe Asp Ile Thr Val Arg Gly Asp Asn
            20                  25                  30 cgt gga tgg ttc aaa gag aac ttt caa aaa gaa aaa atg ata ccg ctt     144
Arg Gly Trp Phe Lys Glu Asn Phe Gln Lys Glu Lys Met Ile Pro Leu
        35                  40                  45 ggt ttc cca gaa agc ttc ttt gag gca gac aaa cta caa aat aat att     192
Gly Phe Pro Glu Ser Phe Phe Glu Ala Asp Lys Leu Gln Asn Asn Ile
 50                  55                  60 tcg ttt aca aaa aaa aat act ttg cga ggt ctc cat gca gag cct tgg     240
Ser Phe Thr Lys Lys Asn Thr Leu Arg Gly Leu His Ala Glu Pro Trp
65                  70                  75                  80 gat aaa tat gtt tcg atc gct gat gaa gga cgt gtg atc ggt act tgg     288
Asp Lys Tyr Val Ser Ile Ala Asp Glu Gly Arg Val Ile Gly Thr Trp
                85                  90                  95 gtt gac ctc cgt gaa ggt gac agt ttt ggt aac gtt tac caa acg att     336
Val Asp Leu Arg Glu Gly Asp Ser Phe Gly Asn Val Tyr Gln Thr Ile
```

-continued

```
              100                 105                 110
atc gat gcc tca aaa ggt att ttt gtt cca cgc ggc gtt gct aat ggt    384
Ile Asp Ala Ser Lys Gly Ile Phe Val Pro Arg Gly Val Ala Asn Gly
            115                 120                 125 ttc caa gtt ctt tca gat aaa gca gct tat act tat ctc gtt aac gat    432
Phe Gln Val Leu Ser Asp Lys Ala Ala Tyr Thr Tyr Leu Val Asn Asp
        130                 135                 140 tat tgg gca ctt gaa ctc aaa cca aaa tat gct ttc gtt aac tat gca    480
Tyr Trp Ala Leu Glu Leu Lys Pro Lys Tyr Ala Phe Val Asn Tyr Ala
145                 150                 155                 160 gat cca aat cta ggc att cag tgg gaa aat ctw gaa gaa gca gaa gtc    528
Asp Pro Asn Leu Gly Ile Gln Trp Glu Asn Leu Glu Glu Ala Glu Val
                165                 170                 175 tca gaa gca gat aag aat cac cca ctt ctc aaa gat gta aaa cct ttg    576
Ser Glu Ala Asp Lys Asn His Pro Leu Leu Lys Asp Val Lys Pro Leu
            180                 185                 190 aag aag gaa gat ttg taa                                            594
Lys Lys Glu Asp Leu
        195
```

<210> SEQ ID NO 8
<211> LENGTH: 197
<212> TYPE: PRT
<213> ORGANISM: Streptococcus agalactiae

<400> SEQUENCE: 8

```
Met Thr Glu Pro Phe Phe Asp Lys Glu Leu Thr Cys Arg Pro Ile Glu
1               5                   10                  15

Ala Ile Pro Glu Leu Leu Glu Phe Asp Ile Thr Val Arg Gly Asp Asn
            20                  25                  30

Arg Gly Trp Phe Lys Glu Asn Phe Gln Lys Glu Lys Met Ile Pro Leu
        35                  40                  45

Gly Phe Pro Glu Ser Phe Glu Ala Asp Lys Leu Gln Asn Asn Ile
    50                  55                  60

Ser Phe Thr Lys Lys Asn Thr Leu Arg Gly Leu His Ala Glu Pro Trp
65                  70                  75                  80

Asp Lys Tyr Val Ser Ile Ala Asp Glu Gly Arg Val Ile Gly Thr Trp
                85                  90                  95

Val Asp Leu Arg Glu Gly Asp Ser Phe Gly Asn Val Tyr Gln Thr Ile
            100                 105                 110

Ile Asp Ala Ser Lys Gly Ile Phe Val Pro Arg Gly Val Ala Asn Gly
        115                 120                 125

Phe Gln Val Leu Ser Asp Lys Ala Ala Tyr Thr Tyr Leu Val Asn Asp
    130                 135                 140

Tyr Trp Ala Leu Glu Leu Lys Pro Lys Tyr Ala Phe Val Asn Tyr Ala
145                 150                 155                 160

Asp Pro Asn Leu Gly Ile Gln Trp Glu Asn Leu Glu Glu Ala Glu Val
                165                 170                 175

Ser Glu Ala Asp Lys Asn His Pro Leu Leu Lys Asp Val Lys Pro Leu
            180                 185                 190

Lys Lys Glu Asp Leu
        195
```

<210> SEQ ID NO 9
<211> LENGTH: 1217
<212> TYPE: DNA
<213> ORGANISM: Streptococcus agalactiae
<220> FEATURE:

<221> NAME/KEY: misc_feature
<222> LOCATION: (571)..(571)
<223> OTHER INFORMATION: N can be A, G, C, or T.
<221> NAME/KEY: CDS
<222> LOCATION: (1)..(570)
<223> OTHER INFORMATION:
<221> NAME/KEY: CDS
<222> LOCATION: (679)..(945)
<223> OTHER INFORMATION:

<400> SEQUENCE: 9

| | | | | | | | | | | | | | | | | |
|---|---|---|---|---|---|---|---|---|---|---|---|---|---|---|---|---|
| tat | tat | tta | atc | gga | ggg | ttg | gca | gaa | atg | caa | cat | gtc | aat | cat | tct | 48 |
| Tyr | Tyr | Leu | Ile | Gly | Gly | Leu | Ala | Glu | Met | Gln | His | Val | Asn | His | Ser | |
| 1 | | | | 5 | | | | | 10 | | | | | 15 | | |
| tct | ttt | gat | aaa | gca | tca | aaa | gca | gga | ttt | att | att | gct | tta | ggc | att | 96 |
| Ser | Phe | Asp | Lys | Ala | Ser | Lys | Ala | Gly | Phe | Ile | Ile | Ala | Leu | Gly | Ile | |
| | | | 20 | | | | | 25 | | | | | 30 | | | |
| gtt | tat | gga | gat | att | ggt | aca | agc | cca | ctc | tat | acg | atg | caa | tca | ttg | 144 |
| Val | Tyr | Gly | Asp | Ile | Gly | Thr | Ser | Pro | Leu | Tyr | Thr | Met | Gln | Ser | Leu | |
| | | 35 | | | | | 40 | | | | | 45 | | | | |
| gtt | gaa | aac | caa | ggt | ggt | att | tct | agt | gtc | aca | gaa | tcg | ttt | atc | tta | 192 |
| Val | Glu | Asn | Gln | Gly | Gly | Ile | Ser | Ser | Val | Thr | Glu | Ser | Phe | Ile | Leu | |
| | 50 | | | | | 55 | | | | | 60 | | | | | |
| ggt | tct | ata | tct | tta | atc | ata | tgg | acc | ttg | aca | ctt | att | aca | act | atc | 240 |
| Gly | Ser | Ile | Ser | Leu | Ile | Ile | Trp | Thr | Leu | Thr | Leu | Ile | Thr | Thr | Ile | |
| 65 | | | | 70 | | | | | 75 | | | | | 80 | | |
| aag | tat | gtg | ctt | gta | gct | tta | aag | gcg | gat | aat | cac | cac | gaa | ggt | ggt | 288 |
| Lys | Tyr | Val | Leu | Val | Ala | Leu | Lys | Ala | Asp | Asn | His | His | Glu | Gly | Gly | |
| | | | | 85 | | | | | 90 | | | | | 95 | | |
| att | ttt | tct | tta | tat | acc | ctt | gtt | aga | aaa | atg | aca | cct | tgg | tta | att | 336 |
| Ile | Phe | Ser | Leu | Tyr | Thr | Leu | Val | Arg | Lys | Met | Thr | Pro | Trp | Leu | Ile | |
| | | | 100 | | | | | 105 | | | | | 110 | | | |
| gtt | ccg | gct | gtt | att | gga | ggt | gca | acc | ttg | ttg | tca | gat | gga | gct | ttg | 384 |
| Val | Pro | Ala | Val | Ile | Gly | Gly | Ala | Thr | Leu | Leu | Ser | Asp | Gly | Ala | Leu | |
| | | 115 | | | | | 120 | | | | | 125 | | | | |
| acg | cca | gct | gta | acc | gta | ctt | cag | ccg | tta | agg | att | aaa | gta | gtt | cct | 432 |
| Thr | Pro | Ala | Val | Thr | Val | Leu | Gln | Pro | Leu | Arg | Ile | Lys | Val | Val | Pro | |
| | 130 | | | | | 135 | | | | | 140 | | | | | |
| agt | ttg | cag | cat | att | tcc | aga | atc | aga | gta | tgt | tat | ttt | gcg | acc | ttg | 480 |
| Ser | Leu | Gln | His | Ile | Ser | Arg | Ile | Arg | Val | Cys | Tyr | Phe | Ala | Thr | Leu | |
| 145 | | | | 150 | | | | | 155 | | | | | 160 | | |
| tta | ttt | act | gtt | act | ttt | gcc | atc | caa | ggt | ttg | gaa | cgg | gtg | tta | ttg | 528 |
| Leu | Phe | Thr | Val | Thr | Phe | Ala | Ile | Gln | Gly | Leu | Glu | Arg | Val | Leu | Leu | |
| | | | | 165 | | | | | 170 | | | | | 175 | | |
| gaa | tta | ttg | gcc | att | atg | tta | tat | ggt | ttg | cct | ttt | ggt | tta | | | 570 |
| Glu | Leu | Leu | Ala | Ile | Met | Leu | Tyr | Gly | Leu | Pro | Phe | Gly | Leu | | | |
| | | | 180 | | | | | 185 | | | | | 190 | | | |

| | | | | |
|---|---|---|---|---|
| ncggtctcct | tatagttttg | cccatccaga | agttttcaag | cattaatcca tactacggtt | 630 |
| tgaaattgtt | atttagtcca | gagaatcata | aaggtatttt | tattttag gat cta ttt | 687 |
| | | | | Asp Leu Phe | |

| | | | | | | | | | | | | | | | | |
|---|---|---|---|---|---|---|---|---|---|---|---|---|---|---|---|---|
| tcc | tgg | cga | caa | acg | gga | gca | gaa | gca | cta | tac | tct | gac | tta | ggt | cat | 735 |
| Ser | Trp | Arg | Gln | Thr | Gly | Ala | Glu | Ala | Leu | Tyr | Ser | Asp | Leu | Gly | His | |
| | 195 | | | | | 200 | | | | | 205 | | | | | |
| gtt | ggg | cgt | gga | aat | ata | cat | gtt | tca | tgg | ccg | ttc | gtt | aag | gtt | gcc | 783 |
| Val | Gly | Arg | Gly | Asn | Ile | His | Val | Ser | Trp | Pro | Phe | Val | Lys | Val | Ala | |
| 210 | | | | 215 | | | | | 220 | | | | | 225 | | |
| att | ata | ctt | tct | tat | tgt | ggg | caa | ggg | gca | tgg | att | tta | gct | aat | aag | 831 |
| Ile | Ile | Leu | Ser | Tyr | Cys | Gly | Gln | Gly | Ala | Trp | Ile | Leu | Ala | Asn | Lys | |
| | | | | 230 | | | | | 235 | | | | | 240 | | |
| aac | gca | gga | aat | gaa | ttg | aat | ccc | ttt | ttt | gct | agt | att | cct | tcg | caa | 879 |
| Asn | Ala | Gly | Asn | Glu | Leu | Asn | Pro | Phe | Phe | Ala | Ser | Ile | Pro | Ser | Gln | |

```
                    245                 250                 255
ttt aca atg cat gtc gtt att tta gct act ttg gca gct atc atc gct      927
Phe Thr Met His Val Val Ile Leu Ala Thr Leu Ala Ala Ile Ile Ala
        260                 265                 270 tca cag gca ctg att tct ggatcaattt accttaagtt ctgagctatg             975
Ser Gln Ala Leu Ile Ser
        275 cgactaaaaa tattcccaca atttcgttca acttatcctg ttgacaatat tgggtcaaac   1035 ctacatacct ggtattaatt ggttcttatt tgccattaca acctctattg gtttgctttt   1095 taagacttca gcgcacatgg aagcagcata tggattagcg ataacaatta cgatgctaat   1155 gacaactatt ttactgtctt tcttttaat tcaaaagga gtaaagagag gttttagcta    1215 tt                                                                  1217
```

<210> SEQ ID NO 10
<211> LENGTH: 190
<212> TYPE: PRT
<213> ORGANISM: Streptococcus agalactiae

<400> SEQUENCE: 10

Tyr Tyr Leu Ile Gly Gly Leu Ala Glu Met Gln His Val Asn His Ser
1               5                   10                  15

Ser Phe Asp Lys Ala Ser Lys Ala Gly Phe Ile Ile Ala Leu Gly Ile
            20                  25                  30

Val Tyr Gly Asp Ile Gly Thr Ser Pro Leu Tyr Thr Met Gln Ser Leu
        35                  40                  45

Val Glu Asn Gln Gly Gly Ile Ser Ser Val Thr Glu Ser Phe Ile Leu
    50                  55                  60

Gly Ser Ile Ser Leu Ile Ile Trp Thr Leu Thr Leu Ile Thr Thr Ile
65                  70                  75                  80

Lys Tyr Val Leu Val Ala Leu Lys Ala Asp Asn His His Glu Gly Gly
                85                  90                  95

Ile Phe Ser Leu Tyr Thr Leu Val Arg Lys Met Thr Pro Trp Leu Ile
            100                 105                 110

Val Pro Ala Val Ile Gly Gly Ala Thr Leu Leu Ser Asp Gly Ala Leu
        115                 120                 125

Thr Pro Ala Val Thr Val Leu Gln Pro Leu Arg Ile Lys Val Val Pro
    130                 135                 140

Ser Leu Gln His Ile Ser Arg Ile Arg Val Cys Tyr Phe Ala Thr Leu
145                 150                 155                 160

Leu Phe Thr Val Thr Phe Ala Ile Gln Gly Leu Glu Arg Val Leu Leu
                165                 170                 175

Glu Leu Leu Ala Ile Met Leu Tyr Gly Leu Pro Phe Gly Leu
            180                 185                 190

<210> SEQ ID NO 11
<211> LENGTH: 89
<212> TYPE: PRT
<213> ORGANISM: Streptococcus agalactiae

<400> SEQUENCE: 11

Asp Leu Phe Ser Trp Arg Gln Thr Gly Ala Glu Ala Leu Tyr Ser Asp
1               5                   10                  15

Leu Gly His Val Gly Arg Gly Asn Ile His Val Ser Trp Pro Phe Val
            20                  25                  30

Lys Val Ala Ile Ile Leu Ser Tyr Cys Gly Gln Gly Ala Trp Ile Leu

-continued

```
                    35                  40                  45
Ala Asn Lys Asn Ala Gly Asn Glu Leu Asn Pro Phe Phe Ala Ser Ile
     50                  55                  60

Pro Ser Gln Phe Thr Met His Val Val Ile Leu Ala Thr Leu Ala Ala
 65                  70                  75                  80

Ile Ile Ala Ser Gln Ala Leu Ile Ser
                 85

<210> SEQ ID NO 12
<211> LENGTH: 378
<212> TYPE: DNA
<213> ORGANISM: Streptococcus agalactiae
<220> FEATURE:
<221> NAME/KEY: CDS
<222> LOCATION: (1)..(378)
<223> OTHER INFORMATION:

<400> SEQUENCE: 12 atg cag gta ttt tta aat att gtc aat aaa ttc ttt gat cca gtt att    48
Met Gln Val Phe Leu Asn Ile Val Asn Lys Phe Phe Asp Pro Val Ile
 1               5                  10                  15 cat atg ggt tcg gga gtt gtg atg cta att gtc atg aca ggt tta gcc    96
His Met Gly Ser Gly Val Val Met Leu Ile Val Met Thr Gly Leu Ala
             20                  25                  30 atg ata ttt gga gtg aag ttt tct aaa gca ctt gaa ggt ggt att aag   144
Met Ile Phe Gly Val Lys Phe Ser Lys Ala Leu Glu Gly Gly Ile Lys
         35                  40                  45 tta gct att gct ctt acg ggt att ggt gct att att ggt att tta act   192
Leu Ala Ile Ala Leu Thr Gly Ile Gly Ala Ile Ile Gly Ile Leu Thr
     50                  55                  60 ggt gct ttt tcc gaa tca ctt caa gct ttt gtt aaa aat aca gga atc   240
Gly Ala Phe Ser Glu Ser Leu Gln Ala Phe Val Lys Asn Thr Gly Ile
 65                  70                  75                  80 aat cta agc att att gac gtt ggt tgg gct cca tta gca act att aca   288
Asn Leu Ser Ile Ile Asp Val Gly Trp Ala Pro Leu Ala Thr Ile Thr
                 85                  90                  95 tgg gga tca cca tat acg ctt tac ttc tta tta atc atg ctt att gtc   336
Trp Gly Ser Pro Tyr Thr Leu Tyr Phe Leu Leu Ile Met Leu Ile Val
            100                 105                 110 aat att gtt atg att gtt atg aaa aaa aaa cgg ata cct tag           378
Asn Ile Val Met Ile Val Met Lys Lys Lys Arg Ile Pro
        115                 120                 125

<210> SEQ ID NO 13
<211> LENGTH: 125
<212> TYPE: PRT
<213> ORGANISM: Streptococcus agalactiae

<400> SEQUENCE: 13

Met Gln Val Phe Leu Asn Ile Val Asn Lys Phe Phe Asp Pro Val Ile
 1               5                  10                  15

His Met Gly Ser Gly Val Val Met Leu Ile Val Met Thr Gly Leu Ala
             20                  25                  30

Met Ile Phe Gly Val Lys Phe Ser Lys Ala Leu Glu Gly Gly Ile Lys
         35                  40                  45

Leu Ala Ile Ala Leu Thr Gly Ile Gly Ala Ile Ile Gly Ile Leu Thr
     50                  55                  60

Gly Ala Phe Ser Glu Ser Leu Gln Ala Phe Val Lys Asn Thr Gly Ile
 65                  70                  75                  80

Asn Leu Ser Ile Ile Asp Val Gly Trp Ala Pro Leu Ala Thr Ile Thr
```

```
                       85                  90                  95
Trp Gly Ser Pro Tyr Thr Leu Tyr Phe Leu Leu Ile Met Leu Ile Val
            100                 105                 110
Asn Ile Val Met Ile Val Met Lys Lys Lys Arg Ile Pro
            115                 120                 125

<210> SEQ ID NO 14
<211> LENGTH: 705
<212> TYPE: DNA
<213> ORGANISM: Streptococcus agalactiae
<220> FEATURE:
<221> NAME/KEY: CDS
<222> LOCATION: (118)..(705)
<223> OTHER INFORMATION:

<400> SEQUENCE: 14
ggatcgggcg caagcttaac gattctttt  aaaatcatta aattttaaaa caaatttcag      60
acatattgcc aaagtttga tattattact ataatatagt ttgtagagga gaataat         117 atg ggc caa gaa cct atc atc gaa tat caa aat atc aat aaa gtg tat      165
Met Gly Gln Glu Pro Ile Ile Glu Tyr Gln Asn Ile Asn Lys Val Tyr
1               5                   10                  15 ggg gaa aat gtt gcg gtt gaa gat att aac ctt aaa att tac cct ggt      213
Gly Glu Asn Val Ala Val Glu Asp Ile Asn Leu Lys Ile Tyr Pro Gly
                20                  25                  30 gat ttc gtt tgt ttc atc ggt acg agt gga tca ggt aaa aca aca tta      261
Asp Phe Val Cys Phe Ile Gly Thr Ser Gly Ser Gly Lys Thr Thr Leu
            35                  40                  45 atg cgt atg gtt aac cat atg tta aaa cca aca aat ggt act cta tta      309
Met Arg Met Val Asn His Met Leu Lys Pro Thr Asn Gly Thr Leu Leu
        50                  55                  60 ttt aag gga aaa gat atc tct act att aac ccc att gaa tta aga cgc      357
Phe Lys Gly Lys Asp Ile Ser Thr Ile Asn Pro Ile Glu Leu Arg Arg
65                  70                  75                  80 aga att gga tat gtt atc caa aac att ggt tta atg cct cat atg acc      405
Arg Ile Gly Tyr Val Ile Gln Asn Ile Gly Leu Met Pro His Met Thr
                85                  90                  95 att tac gaa aat ata gtt ctt gta cca aaa tta ttg aaa tgg tca gaa      453
Ile Tyr Glu Asn Ile Val Leu Val Pro Lys Leu Leu Lys Trp Ser Glu
            100                 105                 110 gaa gct aaa aga gct aaa gca agg gaa ctt att aaa tta gtt gaa tta      501
Glu Ala Lys Arg Ala Lys Ala Arg Glu Leu Ile Lys Leu Val Glu Leu
        115                 120                 125 ccc gaa gaa tat ttg gat cgc tac cct agt gag ttg tct ggc ggt cag      549
Pro Glu Glu Tyr Leu Asp Arg Tyr Pro Ser Glu Leu Ser Gly Gly Gln
130                 135                 140 caa caa cgt atc ggt gtc att cgc gct ctt gca gca gac caa gat att      597
Gln Gln Arg Ile Gly Val Ile Arg Ala Leu Ala Ala Asp Gln Asp Ile
145                 150                 155                 160 att tta atg gat gag cct ttt gga gct ctg gat cct att act aga gaa      645
Ile Leu Met Asp Glu Pro Phe Gly Ala Leu Asp Pro Ile Thr Arg Glu
                165                 170                 175 ggt att caa gac ttt agt caa gtc tct tca gga aga aat ggg gga aaa      693
Gly Ile Gln Asp Phe Ser Gln Val Ser Ser Gly Arg Asn Gly Gly Lys
            180                 185                 190 cta tca tct tag                                                      705
Leu Ser Ser
        195

<210> SEQ ID NO 15
<211> LENGTH: 195
```

```
<212> TYPE: PRT
<213> ORGANISM: Streptococcus agalactiae

<400> SEQUENCE: 15

Met Gly Gln Glu Pro Ile Ile Glu Tyr Gln Asn Ile Asn Lys Val Tyr
1               5                   10                  15

Gly Glu Asn Val Ala Val Glu Asp Ile Asn Leu Lys Ile Tyr Pro Gly
                20                  25                  30

Asp Phe Val Cys Phe Ile Gly Thr Ser Gly Ser Gly Lys Thr Thr Leu
            35                  40                  45

Met Arg Met Val Asn His Met Leu Lys Pro Thr Asn Gly Thr Leu Leu
    50                  55                  60

Phe Lys Gly Lys Asp Ile Ser Thr Ile Asn Pro Ile Glu Leu Arg Arg
65                  70                  75                  80

Arg Ile Gly Tyr Val Ile Gln Asn Ile Gly Leu Met Pro His Met Thr
                85                  90                  95

Ile Tyr Glu Asn Ile Val Leu Val Pro Lys Leu Leu Lys Trp Ser Glu
                100                 105                 110

Glu Ala Lys Arg Ala Lys Ala Arg Glu Leu Ile Lys Leu Val Glu Leu
            115                 120                 125

Pro Glu Glu Tyr Leu Asp Arg Tyr Pro Ser Glu Leu Ser Gly Gly Gln
    130                 135                 140

Gln Gln Arg Ile Gly Val Ile Arg Ala Leu Ala Ala Asp Gln Asp Ile
145                 150                 155                 160

Ile Leu Met Asp Glu Pro Phe Gly Ala Leu Asp Pro Ile Thr Arg Glu
                165                 170                 175

Gly Ile Gln Asp Phe Ser Gln Val Ser Ser Gly Arg Asn Gly Gly Lys
                180                 185                 190

Leu Ser Ser
        195

<210> SEQ ID NO 16
<211> LENGTH: 367
<212> TYPE: DNA
<213> ORGANISM: Streptococcus agalactiae
<220> FEATURE:
<221> NAME/KEY: CDS
<222> LOCATION: (1)..(366)
<223> OTHER INFORMATION:

<400> SEQUENCE: 16 atc cct tat agt gat gtt ttt gct aca gga gga ttt tta tac tat gta      48
Ile Pro Tyr Ser Asp Val Phe Ala Thr Gly Gly Phe Leu Tyr Tyr Val
1               5                   10                  15 acg att gct cta agt tac ctt tta ggg tct agt atc tgg tta ttt att      96
Thr Ile Ala Leu Ser Tyr Leu Leu Gly Ser Ser Ile Trp Leu Phe Ile
                20                  25                  30 gta cag ttt att gct tac tat gta tct gga att tat ttt tat aaa tta     144
Val Gln Phe Ile Ala Tyr Tyr Val Ser Gly Ile Tyr Phe Tyr Lys Leu
            35                  40                  45 gtt tat tat gtg gca caa agt gaa att gtc tcg ata ggc atg acg ttg     192
Val Tyr Tyr Val Ala Gln Ser Glu Ile Val Ser Ile Gly Met Thr Leu
    50                  55                  60 att ttc tat ata atg aat att gtc tta gga ttc ggt ggt atg tac cca     240
Ile Phe Tyr Ile Met Asn Ile Val Leu Gly Phe Gly Gly Met Tyr Pro
65                  70                  75                  80 ata cag tgg gca tta cct ttt atg ctc att tcg cta tgg ttt tta att     288
Ile Gln Trp Ala Leu Pro Phe Met Leu Ile Ser Leu Trp Phe Leu Ile
                85                  90                  95
```

```
aaa ttt tgt gtc gat aat atc gtt gat gaa gca ttt ata ttt tat ggt         336
Lys Phe Cys Val Asp Asn Ile Val Asp Glu Ala Phe Ile Phe Tyr Gly
            100                 105                 110 att tta gca gca ttc tca cta ttt ata gat c                               367
Ile Leu Ala Ala Phe Ser Leu Phe Ile Asp
        115                 120

<210> SEQ ID NO 17
<211> LENGTH: 122
<212> TYPE: PRT
<213> ORGANISM: Streptococcus agalactiae

<400> SEQUENCE: 17

Ile Pro Tyr Ser Asp Val Phe Ala Thr Gly Gly Phe Leu Tyr Tyr Val
1               5                   10                  15

Thr Ile Ala Leu Ser Tyr Leu Leu Gly Ser Ser Ile Trp Leu Phe Ile
            20                  25                  30

Val Gln Phe Ile Ala Tyr Tyr Val Ser Gly Ile Tyr Phe Tyr Lys Leu
        35                  40                  45

Val Tyr Tyr Val Ala Gln Ser Glu Ile Val Ser Ile Gly Met Thr Leu
50                  55                  60

Ile Phe Tyr Ile Met Asn Ile Val Leu Gly Phe Gly Gly Met Tyr Pro
65                  70                  75                  80

Ile Gln Trp Ala Leu Pro Phe Met Leu Ile Ser Leu Trp Phe Leu Ile
                85                  90                  95

Lys Phe Cys Val Asp Asn Ile Val Asp Glu Ala Phe Ile Phe Tyr Gly
            100                 105                 110

Ile Leu Ala Ala Phe Ser Leu Phe Ile Asp
        115                 120

<210> SEQ ID NO 18
<211> LENGTH: 570
<212> TYPE: DNA
<213> ORGANISM: Streptococcus agalactiae
<220> FEATURE:
<221> NAME/KEY: CDS
<222> LOCATION: (1)..(570)
<223> OTHER INFORMATION:

<400> SEQUENCE: 18 atg agg aaa cgt ttt tcc ttg cta aat ttt att gtt gtt act ttt att         48
Met Arg Lys Arg Phe Ser Leu Leu Asn Phe Ile Val Val Thr Phe Ile
1               5                   10                  15 ttc ttt ttc ttt att ctt ttt ccg ctt tta aac cat aag gga aaa gta         96
Phe Phe Phe Phe Ile Leu Phe Pro Leu Leu Asn His Lys Gly Lys Val
            20                  25                  30 gat gct aat tct agg cag agt gtt acc tac acc aaa gaa gaa ttt ata        144
Asp Ala Asn Ser Arg Gln Ser Val Thr Tyr Thr Lys Glu Glu Phe Ile
        35                  40                  45 caa aaa att gtg cca gat gcg caa gat cta gga aag tcg tac ggt att        192
Gln Lys Ile Val Pro Asp Ala Gln Asp Leu Gly Lys Ser Tyr Gly Ile
50                  55                  60 cgt cct tca ttt att att gca cag gcg gct ttg gat tct gat ttc gga        240
Arg Pro Ser Phe Ile Ile Ala Gln Ala Ala Leu Asp Ser Asp Phe Gly
65                  70                  75                  80 gag aaa tat agc tat agt atc ata atc tgt tgg ttg ctt gca gaa cca        288
Glu Lys Tyr Ser Tyr Ser Ile Ile Ile Cys Trp Leu Leu Ala Glu Pro
                85                  90                  95 gga acg ccc tca att acc tta aat gat agt agt aca gga aaa aaa cag        336
Gly Thr Pro Ser Ile Thr Leu Asn Asp Ser Ser Thr Gly Lys Lys Gln
```

| | | | | | | | | | | | | | | | | |
|---|---|---|---|---|---|---|---|---|---|---|---|---|---|---|---|---|
| | | 100 | | | | 105 | | | | | 110 | | | | | |
| gaa | aag | caa | ttt | act | cat | tat | aaa | tct | tgg | aag | tat | tca | atg | gat | gat | 384 |
| Glu | Lys | Gln | Phe | Thr | His | Tyr | Lys | Ser | Trp | Lys | Tyr | Ser | Met | Asp | Asp | |
| | | 115 | | | | | 120 | | | | | 125 | | | | |
| tac | ctt | gct | cat | ata | aaa | tct | gga | gcg | aca | ggc | aaa | aaa | gat | tca | tat | 432 |
| Tyr | Leu | Ala | His | Ile | Lys | Ser | Gly | Ala | Thr | Gly | Lys | Lys | Asp | Ser | Tyr | |
| | 130 | | | | | 135 | | | | | 140 | | | | | |
| act | ata | atg | gtg | tct | gtt | aaa | aat | cca | aaa | act | tta | gtg | caa | aaa | tta | 480 |
| Thr | Ile | Met | Val | Ser | Val | Lys | Asn | Pro | Lys | Thr | Leu | Val | Gln | Lys | Leu | |
| 145 | | | | | 150 | | | | | 155 | | | | | 160 | |
| caa | gat | agt | ggt | ttt | gat | aat | gac | aaa | aag | tac | gct | aaa | aaa | atg | acg | 528 |
| Gln | Asp | Ser | Gly | Phe | Asp | Asn | Asp | Lys | Lys | Tyr | Ala | Lys | Lys | Met | Thr | |
| | | | | 165 | | | | | 170 | | | | | 175 | | |
| gaa | atc | att | gat | ttg | tat | gat | tta | aca | aga | tat | gat | aag | tga | | | 570 |
| Glu | Ile | Ile | Asp | Leu | Tyr | Asp | Leu | Thr | Arg | Tyr | Asp | Lys | | | | |
| | | | 180 | | | | | 185 | | | | | | | | |

<210> SEQ ID NO 19
<211> LENGTH: 189
<212> TYPE: PRT
<213> ORGANISM: Streptococcus agalactiae

<400> SEQUENCE: 19

Met Arg Lys Arg Phe Ser Leu Leu Asn Phe Ile Val Val Thr Phe Ile
1               5                   10                  15

Phe Phe Phe Phe Ile Leu Phe Pro Leu Leu Asn His Lys Gly Lys Val
                20                  25                  30

Asp Ala Asn Ser Arg Gln Ser Val Thr Tyr Thr Lys Glu Glu Phe Ile
            35                  40                  45

Gln Lys Ile Val Pro Asp Ala Gln Asp Leu Gly Lys Ser Tyr Gly Ile
        50                  55                  60

Arg Pro Ser Phe Ile Ile Ala Gln Ala Ala Leu Asp Ser Asp Phe Gly
65                  70                  75                  80

Glu Lys Tyr Ser Tyr Ser Ile Ile Ile Cys Trp Leu Leu Ala Glu Pro
                85                  90                  95

Gly Thr Pro Ser Ile Thr Leu Asn Asp Ser Ser Thr Gly Lys Lys Gln
                100                 105                 110

Glu Lys Gln Phe Thr His Tyr Lys Ser Trp Lys Tyr Ser Met Asp Asp
            115                 120                 125

Tyr Leu Ala His Ile Lys Ser Gly Ala Thr Gly Lys Lys Asp Ser Tyr
        130                 135                 140

Thr Ile Met Val Ser Val Lys Asn Pro Lys Thr Leu Val Gln Lys Leu
145                 150                 155                 160

Gln Asp Ser Gly Phe Asp Asn Asp Lys Lys Tyr Ala Lys Lys Met Thr
                165                 170                 175

Glu Ile Ile Asp Leu Tyr Asp Leu Thr Arg Tyr Asp Lys
            180                 185

<210> SEQ ID NO 20
<211> LENGTH: 978
<212> TYPE: DNA
<213> ORGANISM: Streptococcus agalactiae
<220> FEATURE:
<221> NAME/KEY: CDS
<222> LOCATION: (1)..(978)
<223> OTHER INFORMATION:

<400> SEQUENCE: 20 atg ctt gtc atc att ttg atc att gta cta gct agt ctg aca gtg acg     48

```
                                                    -continued

Met Leu Val Ile Ile Leu Ile Ile Val Leu Ala Ser Leu Thr Val Thr
1               5                   10                  15 ata att tct tac cca aaa atg acg gaa tta aca aag tcc gtt gaa aaa              96
Ile Ile Ser Tyr Pro Lys Met Thr Glu Leu Thr Lys Ser Val Glu Lys
            20                  25                  30 caa ctt gaa gat aat gct gat aat cta tca gac caa ctg aca tat cag            144
Gln Leu Glu Asp Asn Ala Asp Asn Leu Ser Asp Gln Leu Thr Tyr Gln
        35                  40                  45 ata gaa gtg gcg caa aaa gat caa atc tac gtg act aat cag cta aac            192
Ile Glu Val Ala Gln Lys Asp Gln Ile Tyr Val Thr Asn Gln Leu Asn
50                  55                  60 cgt atg caa cag gaa att atc agt cgc tta ccg ata tgc gta cag aat            240
Arg Met Gln Gln Glu Ile Ile Ser Arg Leu Pro Ile Cys Val Gln Asn
65                  70                  75                  80 aaa tca gca tta acg gag agt cga gat cga tca gac aaa cgc ttg gaa            288
Lys Ser Ala Leu Thr Glu Ser Arg Asp Arg Ser Asp Lys Arg Leu Glu
            85                  90                  95 ttg att aac tcc aat tta tct cag tca gtt cag aaa atg caa gat tca            336
Leu Ile Asn Ser Asn Leu Ser Gln Ser Val Gln Lys Met Gln Asp Ser
        100                 105                 110 atg aaa aac gct tgg atc aaa tgc gcc aaa ctg ttg agg aaa agc tgg            384
Met Lys Asn Ala Trp Ile Lys Cys Ala Lys Leu Leu Arg Lys Ser Trp
            115                 120                 125 aaa aaa cgc tac aaa cgc gtt gca aac ttc ttt gaa act gta tcg cgt            432
Lys Lys Arg Tyr Lys Arg Val Ala Asn Phe Phe Glu Thr Val Ser Arg
130                 135                 140 caa cta gag agc gtc aat caa ggt ctg ggt aga tgg aaa ctg tgc caa            480
Gln Leu Glu Ser Val Asn Gln Gly Leu Gly Arg Trp Lys Leu Cys Gln
145                 150                 155                 160 gat gtt ggt acc act gaa caa agt ctg tca aat act aag aca agg gga            528
Asp Val Gly Thr Thr Glu Gln Ser Leu Ser Asn Thr Lys Thr Arg Gly
            165                 170                 175 ata tta ggg gag tta caa ctc ggt caa att ata gaa gat att atg aca            576
Ile Leu Gly Glu Leu Gln Leu Gly Gln Ile Ile Glu Asp Ile Met Thr
        180                 185                 190 gtt agt caa tat gag aga gaa ttt cct acg gtg tct ggc tct tct gag            624
Val Ser Gln Tyr Glu Arg Glu Phe Pro Thr Val Ser Gly Ser Ser Glu
            195                 200                 205 cgt gtt gaa tat gct att aaa tac ctg gaa atg gtc agg gag att ata            672
Arg Val Glu Tyr Ala Ile Lys Tyr Leu Glu Met Val Arg Glu Ile Ile
210                 215                 220 tct att tgc cta ttg act cta agt ttc tct aga aga tta tta ccg att            720
Ser Ile Cys Leu Leu Thr Leu Ser Phe Ser Arg Arg Leu Leu Pro Ile
225                 230                 235                 240 ggg aga tgc tta tgg aat tgg gtg acc agg ttc aaa tgg aac tct att            768
Gly Arg Cys Leu Trp Asn Trp Val Thr Arg Phe Lys Trp Asn Ser Ile
            245                 250                 255 cgt aat ctt tac tgg gca agt att cgt aaa ttt gca aaa gat ata aac            816
Arg Asn Leu Tyr Trp Ala Ser Ile Arg Lys Phe Ala Lys Asp Ile Asn
        260                 265                 270 aat aag tac tta aat cct cct gaa acg aca aat ttt ggt atc atg ttc            864
Asn Lys Tyr Leu Asn Pro Pro Glu Thr Thr Asn Phe Gly Ile Met Phe
            275                 280                 285 tta cca act gaa ggg ctc tat tct gaa gtg gta aga aat gca aca ttc            912
Leu Pro Thr Glu Gly Leu Tyr Ser Glu Val Val Arg Asn Ala Thr Phe
290                 295                 300 ttt gat agt cta aga cgt gac gaa aat att gta gta gct gga ccg tca            960
Phe Asp Ser Leu Arg Arg Asp Glu Asn Ile Val Val Ala Gly Pro Ser
305                 310                 315                 320
```

```
acc tta tct gct tac taa                                              978
Thr Leu Ser Ala Tyr
            325

<210> SEQ ID NO 21
<211> LENGTH: 325
<212> TYPE: PRT
<213> ORGANISM: Streptococcus agalactiae

<400> SEQUENCE: 21

Met Leu Val Ile Ile Leu Ile Ile Val Leu Ala Ser Leu Thr Val Thr
1               5                   10                  15

Ile Ile Ser Tyr Pro Lys Met Thr Glu Leu Thr Lys Ser Val Glu Lys
            20                  25                  30

Gln Leu Glu Asp Asn Ala Asp Asn Leu Ser Asp Gln Leu Thr Tyr Gln
        35                  40                  45

Ile Glu Val Ala Gln Lys Asp Gln Ile Tyr Val Thr Asn Gln Leu Asn
    50                  55                  60

Arg Met Gln Gln Glu Ile Ile Ser Arg Leu Pro Ile Cys Val Gln Asn
65                  70                  75                  80

Lys Ser Ala Leu Thr Glu Ser Arg Asp Arg Ser Asp Lys Arg Leu Glu
                85                  90                  95

Leu Ile Asn Ser Asn Leu Ser Gln Ser Val Gln Lys Met Gln Asp Ser
            100                 105                 110

Met Lys Asn Ala Trp Ile Lys Cys Ala Lys Leu Leu Arg Lys Ser Trp
        115                 120                 125

Lys Lys Arg Tyr Lys Arg Val Ala Asn Phe Phe Glu Thr Val Ser Arg
    130                 135                 140

Gln Leu Glu Ser Val Asn Gln Gly Leu Gly Arg Trp Lys Leu Cys Gln
145                 150                 155                 160

Asp Val Gly Thr Thr Glu Gln Ser Leu Ser Asn Thr Lys Thr Arg Gly
                165                 170                 175

Ile Leu Gly Glu Leu Gln Leu Gly Gln Ile Ile Glu Asp Ile Met Thr
            180                 185                 190

Val Ser Gln Tyr Glu Arg Glu Phe Pro Thr Val Ser Gly Ser Ser Glu
        195                 200                 205

Arg Val Glu Tyr Ala Ile Lys Tyr Leu Glu Met Val Arg Glu Ile Ile
    210                 215                 220

Ser Ile Cys Leu Leu Thr Leu Ser Phe Ser Arg Arg Leu Leu Pro Ile
225                 230                 235                 240

Gly Arg Cys Leu Trp Asn Trp Val Thr Arg Phe Lys Trp Asn Ser Ile
                245                 250                 255

Arg Asn Leu Tyr Trp Ala Ser Ile Arg Lys Phe Ala Lys Asp Ile Asn
            260                 265                 270

Asn Lys Tyr Leu Asn Pro Pro Glu Thr Thr Asn Phe Gly Ile Met Phe
        275                 280                 285

Leu Pro Thr Glu Gly Leu Tyr Ser Glu Val Val Arg Asn Ala Thr Phe
    290                 295                 300

Phe Asp Ser Leu Arg Arg Asp Glu Asn Ile Val Val Ala Gly Pro Ser
305                 310                 315                 320

Thr Leu Ser Ala Tyr
            325

<210> SEQ ID NO 22
<211> LENGTH: 579
<212> TYPE: DNA
```

```
<213> ORGANISM: Streptococcus agalactiae
<220> FEATURE:
<221> NAME/KEY: CDS
<222> LOCATION: (1)..(579)
<223> OTHER INFORMATION:

<400> SEQUENCE: 22 atg cga aaa gaa gtg aca cca gag atg ctt aac tat aat aag tat cct      48
Met Arg Lys Glu Val Thr Pro Glu Met Leu Asn Tyr Asn Lys Tyr Pro
1               5                  10                  15 ggc cca cag ttt att cac ttt gaa aat atc gtt aaa agt gat gat att      96
Gly Pro Gln Phe Ile His Phe Glu Asn Ile Val Lys Ser Asp Asp Ile
            20                  25                  30 gaa ttt caa ctt gtt att aat gaa aaa tca gct ttt gat gtg act gtc     144
Glu Phe Gln Leu Val Ile Asn Glu Lys Ser Ala Phe Asp Val Thr Val
        35                  40                  45 ttt gga caa cgt ttt tct gag att tta tta aaa tat gat ttt atc gtt     192
Phe Gly Gln Arg Phe Ser Glu Ile Leu Leu Lys Tyr Asp Phe Ile Val
    50                  55                  60 ggc gat tgg ggt aac gag cag ttg agg cta aga ggc ttt tac aaa gat     240
Gly Asp Trp Gly Asn Glu Gln Leu Arg Leu Arg Gly Phe Tyr Lys Asp
65                  70                  75                  80 gct agt acg att aga aaa aat agc cgg att tca cgt tta gaa gat tat     288
Ala Ser Thr Ile Arg Lys Asn Ser Arg Ile Ser Arg Leu Glu Asp Tyr
                85                  90                  95 att aaa gag tat tgt aac ttt ggt tgt gct tat ttt gtg ttg gag aat     336
Ile Lys Glu Tyr Cys Asn Phe Gly Cys Ala Tyr Phe Val Leu Glu Asn
            100                 105                 110 cca aat cct aga gat att aaa ttt gat gat gaa aga cct cat aag cgt     384
Pro Asn Pro Arg Asp Ile Lys Phe Asp Asp Glu Arg Pro His Lys Arg
        115                 120                 125 cgt aag tca aga tcc aaa tca caa tca tca aag tca caa act aga aat     432
Arg Lys Ser Arg Ser Lys Ser Gln Ser Ser Lys Ser Gln Thr Arg Asn
    130                 135                 140 aat cgt tcc cag tca aat gcc aat gct cat ttt aca agt aaa aag cgt     480
Asn Arg Ser Gln Ser Asn Ala Asn Ala His Phe Thr Ser Lys Lys Arg
145                 150                 155                 160 aaa gac aca aaa cgc cgt caa gaa cgt cat att aaa gaa gag caa gat     528
Lys Asp Thr Lys Arg Arg Gln Glu Arg His Ile Lys Glu Glu Gln Asp
                165                 170                 175 aag gaa atg acc tct gca aag cag cat ttg tta ttc gta aga aaa aat     576
Lys Glu Met Thr Ser Ala Lys Gln His Leu Leu Phe Val Arg Lys Asn
            180                 185                 190 taa                                                                  579

<210> SEQ ID NO 23
<211> LENGTH: 192
<212> TYPE: PRT
<213> ORGANISM: Streptococcus agalactiae

<400> SEQUENCE: 23

Met Arg Lys Glu Val Thr Pro Glu Met Leu Asn Tyr Asn Lys Tyr Pro
1               5                  10                  15

Gly Pro Gln Phe Ile His Phe Glu Asn Ile Val Lys Ser Asp Asp Ile
            20                  25                  30

Glu Phe Gln Leu Val Ile Asn Glu Lys Ser Ala Phe Asp Val Thr Val
        35                  40                  45

Phe Gly Gln Arg Phe Ser Glu Ile Leu Leu Lys Tyr Asp Phe Ile Val
    50                  55                  60

Gly Asp Trp Gly Asn Glu Gln Leu Arg Leu Arg Gly Phe Tyr Lys Asp
```

```
              65                  70                  75                  80
      Ala Ser Thr Ile Arg Lys Asn Ser Arg Ile Ser Arg Leu Glu Asp Tyr
                          85                  90                  95

Ile Lys Glu Tyr Cys Asn Phe Gly Cys Ala Tyr Phe Val Leu Glu Asn
                         100                 105                 110

Pro Asn Pro Arg Asp Ile Lys Phe Asp Asp Glu Arg Pro His Lys Arg
                     115                 120                 125

Arg Lys Ser Arg Ser Lys Ser Gln Ser Ser Lys Ser Gln Thr Arg Asn
                 130                 135                 140

Asn Arg Ser Gln Ser Asn Ala Asn Ala His Phe Thr Ser Lys Lys Arg
      145                 150                 155                 160

Lys Asp Thr Lys Arg Arg Gln Glu Arg His Ile Lys Glu Gln Asp
                         165                 170                 175

Lys Glu Met Thr Ser Ala Lys Gln His Leu Leu Phe Val Arg Lys Asn
                     180                 185                 190

<210> SEQ ID NO 24
<211> LENGTH: 609
<212> TYPE: DNA
<213> ORGANISM: Streptococcus agalactiae
<220> FEATURE:
<221> NAME/KEY: CDS
<222> LOCATION: (1)..(609)
<223> OTHER INFORMATION:

<400> SEQUENCE: 24 atg aca ata aaa aaa gtg tta agt gta aca gga att att tta gtg aca        48
Met Thr Ile Lys Lys Val Leu Ser Val Thr Gly Ile Ile Leu Val Thr
1               5                  10                  15 gta gcg tct cta gct gct tgt agc tca aaa tct cat act act aag acg        96
Val Ala Ser Leu Ala Ala Cys Ser Ser Lys Ser His Thr Thr Lys Thr
                20                  25                  30 ggc aaa aaa gaa gtt aat ttt gca act gtt gga aca acg gca cct ttt       144
Gly Lys Lys Glu Val Asn Phe Ala Thr Val Gly Thr Thr Ala Pro Phe
            35                  40                  45 tct tat gtg aag gat ggg aaa ctg act ggc ttt gat att gaa gta gcc       192
Ser Tyr Val Lys Asp Gly Lys Leu Thr Gly Phe Asp Ile Glu Val Ala
        50                  55                  60 aaa gct gtt ttt aaa ggt tca gat aac tat aaa gtc act ttt aaa aaa       240
Lys Ala Val Phe Lys Gly Ser Asp Asn Tyr Lys Val Thr Phe Lys Lys
65                  70                  75                  80 aca gaa tgg tca tcg gta ttt acc ggc att gat tca gga aag ttt caa       288
Thr Glu Trp Ser Ser Val Phe Thr Gly Ile Asp Ser Gly Lys Phe Gln
                85                  90                  95 atg ggt gga aat aat att tct tat tca tca gag aga tct caa aaa tay       336
Met Gly Gly Asn Asn Ile Ser Tyr Ser Ser Glu Arg Ser Gln Lys Tyr
            100                 105                 110 tta ttt tca tac cca ata ggc tct act cct tca gtt tta gca gtt cct       384
Leu Phe Ser Tyr Pro Ile Gly Ser Thr Pro Ser Val Leu Ala Val Pro
        115                 120                 125 aag aat agt aat atc aaa gct tat aat gat att agt ggt cat aaa aca       432
Lys Asn Ser Asn Ile Lys Ala Tyr Asn Asp Ile Ser Gly His Lys Thr
130                 135                 140 cag gtt gtc caa gga acg aca act gcc aag caa tta gaa aat ttc aat       480
Gln Val Val Gln Gly Thr Thr Thr Ala Lys Gln Leu Glu Asn Phe Asn
145                 150                 155                 160 aaa gag cat cag aaa aat cct gtt act cta aaa tat act aat gaa aat       528
Lys Glu His Gln Lys Asn Pro Val Thr Leu Lys Tyr Thr Asn Glu Asn
                165                 170                 175
```

-continued

```
att aca cag att cta acg aat ttg agt gat gga aaa gct gat ttt aaa      576
Ile Thr Gln Ile Leu Thr Asn Leu Ser Asp Gly Lys Ala Asp Phe Lys
            180                 185                 190 ctt ttg acg gac caa ctg tta acg cta tta taa                          609
Leu Leu Thr Asp Gln Leu Leu Thr Leu Leu
        195                 200
```

<210> SEQ ID NO 25
<211> LENGTH: 202
<212> TYPE: PRT
<213> ORGANISM: Streptococcus agalactiae

<400> SEQUENCE: 25

```
Met Thr Ile Lys Lys Val Leu Ser Val Thr Gly Ile Ile Leu Val Thr
1               5                   10                  15

Val Ala Ser Leu Ala Ala Cys Ser Ser Lys Ser His Thr Thr Lys Thr
            20                  25                  30

Gly Lys Lys Glu Val Asn Phe Ala Thr Val Gly Thr Thr Ala Pro Phe
        35                  40                  45

Ser Tyr Val Lys Asp Gly Lys Leu Thr Gly Phe Asp Ile Glu Val Ala
    50                  55                  60

Lys Ala Val Phe Lys Gly Ser Asp Asn Tyr Lys Val Thr Phe Lys Lys
65                  70                  75                  80

Thr Glu Trp Ser Ser Val Phe Thr Gly Ile Asp Ser Gly Lys Phe Gln
                85                  90                  95

Met Gly Gly Asn Asn Ile Ser Tyr Ser Ser Glu Arg Ser Gln Lys Tyr
            100                 105                 110

Leu Phe Ser Tyr Pro Ile Gly Ser Thr Pro Ser Val Leu Ala Val Pro
        115                 120                 125

Lys Asn Ser Asn Ile Lys Ala Tyr Asn Asp Ile Ser Gly His Lys Thr
    130                 135                 140

Gln Val Val Gln Gly Thr Thr Thr Ala Lys Gln Leu Glu Asn Phe Asn
145                 150                 155                 160

Lys Glu His Gln Lys Asn Pro Val Thr Leu Lys Tyr Thr Asn Glu Asn
                165                 170                 175

Ile Thr Gln Ile Leu Thr Asn Leu Ser Asp Gly Lys Ala Asp Phe Lys
            180                 185                 190

Leu Leu Thr Asp Gln Leu Leu Thr Leu Leu
        195                 200
```

<210> SEQ ID NO 26
<211> LENGTH: 357
<212> TYPE: DNA
<213> ORGANISM: Streptococcus agalactiae
<220> FEATURE:
<221> NAME/KEY: CDS
<222> LOCATION: (1)..(357)
<223> OTHER INFORMATION:

<400> SEQUENCE: 26

```
atg aag aat ata aca aag cta tca act gtt gct tta agc cta cta ctt      48
Met Lys Asn Ile Thr Lys Leu Ser Thr Val Ala Leu Ser Leu Leu Leu
1               5                   10                  15 tgt acg gcg tgt gct gca tca aac acg tct aca tct aaa aca cag tct      96
Cys Thr Ala Cys Ala Ala Ser Asn Thr Ser Thr Ser Lys Thr Gln Ser
            20                  25                  30 cat cat cct aaa caa act aaa ctc aca gat aag caa aaa gaa gaa ccc      144
His His Pro Lys Gln Thr Lys Leu Thr Asp Lys Gln Lys Glu Glu Pro
        35                  40                  45
```

```
aaa aac aaa gaa gct gct gat caa gag atg cat ccc caa ggc gct gtt     192
Lys Asn Lys Glu Ala Ala Asp Gln Glu Met His Pro Gln Gly Ala Val
     50                  55                  60 gat ttg aca aaa tat aag gca aaa ccg gtc aaa gat tat gga aaa aaa     240
Asp Leu Thr Lys Tyr Lys Ala Lys Pro Val Lys Asp Tyr Gly Lys Lys
 65                  70                  75                  80 atc gat gtt ggt gat ggc aag aaa atg aac att tat gaa act ggt cag     288
Ile Asp Val Gly Asp Gly Lys Lys Met Asn Ile Tyr Glu Thr Gly Gln
                 85                  90                  95 gga aaa att cca att gtt ttt att cct ggt caa gct gag att cgc cac     336
Gly Lys Ile Pro Ile Val Phe Ile Pro Gly Gln Ala Glu Ile Arg His
            100                 105                 110 gct atg ctt ata aga att taa                                         357
Ala Met Leu Ile Arg Ile
            115

<210> SEQ ID NO 27
<211> LENGTH: 118
<212> TYPE: PRT
<213> ORGANISM: Streptococcus agalactiae

<400> SEQUENCE: 27

Met Lys Asn Ile Thr Lys Leu Ser Thr Val Ala Leu Ser Leu Leu Leu
 1               5                  10                  15

Cys Thr Ala Cys Ala Ala Ser Asn Thr Ser Thr Ser Lys Thr Gln Ser
             20                  25                  30

His His Pro Lys Gln Thr Lys Leu Thr Asp Lys Gln Lys Glu Glu Pro
            35                  40                  45

Lys Asn Lys Glu Ala Ala Asp Gln Glu Met His Pro Gln Gly Ala Val
     50                  55                  60

Asp Leu Thr Lys Tyr Lys Ala Lys Pro Val Lys Asp Tyr Gly Lys Lys
 65                  70                  75                  80

Ile Asp Val Gly Asp Gly Lys Lys Met Asn Ile Tyr Glu Thr Gly Gln
                 85                  90                  95

Gly Lys Ile Pro Ile Val Phe Ile Pro Gly Gln Ala Glu Ile Arg His
            100                 105                 110

Ala Met Leu Ile Arg Ile
            115

<210> SEQ ID NO 28
<211> LENGTH: 1191
<212> TYPE: DNA
<213> ORGANISM: Streptococcus agalactiae
<220> FEATURE:
<221> NAME/KEY: CDS
<222> LOCATION: (1)..(1191)
<223> OTHER INFORMATION:

<400> SEQUENCE: 28 gtg aat gaa tcg acc atc aga aaa gaa ttt aaa ata gtt gtt ttt aaa      48
Val Asn Glu Ser Thr Ile Arg Lys Glu Phe Lys Ile Val Val Phe Lys
 1               5                  10                  15 tgg atc tta aat aat caa gca gtt att gct ctc atg att acc ttt ttg      96
Trp Ile Leu Asn Asn Gln Ala Val Ile Ala Leu Met Ile Thr Phe Leu
             20                  25                  30 gta ttt tta acg att ttt att ttt acc aaa atc tct ttt atg ttt aaa     144
Val Phe Leu Thr Ile Phe Ile Phe Thr Lys Ile Ser Phe Met Phe Lys
            35                  40                  45 cct gtg ttt gat ttt ctt gct gtg ctg ata ttg ccg ctt gta att tct     192
Pro Val Phe Asp Phe Leu Ala Val Leu Ile Leu Pro Leu Val Ile Ser
     50                  55                  60
```

```
                                                    -continued ggc ttg ctt tat tac cta tta aaa cct atg gtt aca ttt tta gag aag        240
Gly Leu Leu Tyr Tyr Leu Leu Lys Pro Met Val Thr Phe Leu Glu Lys
65                  70                  75                  80 cgg gga att aag cgt gta aca gcg ata tta tca gtt ttt act att ata        288
Arg Gly Ile Lys Arg Val Thr Ala Ile Leu Ser Val Phe Thr Ile Ile
                85                  90                  95 atc ctt ctg tta att tgg gca atg tct agt ttt att ccc atg atg agt        336
Ile Leu Leu Leu Ile Trp Ala Met Ser Ser Phe Ile Pro Met Met Ser
            100                 105                 110 aat caa tta cgc cat ttt atg gaa gat ctc cct tca tat gtg aat aaa        384
Asn Gln Leu Arg His Phe Met Glu Asp Leu Pro Ser Tyr Val Asn Lys
        115                 120                 125 gtg caa atg gaa aca agt tcg ttt ata gat cac aac cct tgg tta aaa        432
Val Gln Met Glu Thr Ser Ser Phe Ile Asp His Asn Pro Trp Leu Lys
    130                 135                 140 tct tat aaa ggg gaa ata tcg agc atg tta tct aat atc agt agc caa        480
Ser Tyr Lys Gly Glu Ile Ser Ser Met Leu Ser Asn Ile Ser Ser Gln
145                 150                 155                 160 gcg gtc tct tat gct gaa aaa ttt tca aag aat gtt tta gat tgg gca        528
Ala Val Ser Tyr Ala Glu Lys Phe Ser Lys Asn Val Leu Asp Trp Ala
                165                 170                 175 gga aat tta gct agt aca gtt gca cgt gtg aca gta gca aca atc atg        576
Gly Asn Leu Ala Ser Thr Val Ala Arg Val Thr Val Ala Thr Ile Met
            180                 185                 190 gct ccc ttt att ttg ttt tat ctt tta aga gat agt cgc aac atg aag        624
Ala Pro Phe Ile Leu Phe Tyr Leu Leu Arg Asp Ser Arg Asn Met Lys
        195                 200                 205 aat ggt ttc tta atg gtt tta cca acc aaa cta cgc caa cca gct gat        672
Asn Gly Phe Leu Met Val Leu Pro Thr Lys Leu Arg Gln Pro Ala Asp
    210                 215                 220 cgt att ttg cga gaa atg aat agt caa atg tca gga tat gtg caa gga        720
Arg Ile Leu Arg Glu Met Asn Ser Gln Met Ser Gly Tyr Val Gln Gly
225                 230                 235                 240 caa atc att gtt gct att act gtt ggt gtt att ttt tca ata atg tat        768
Gln Ile Ile Val Ala Ile Thr Val Gly Val Ile Phe Ser Ile Met Tyr
                245                 250                 255 agt att ata ggc ctt aga tat ggc gtg aca tta ggg att att gcc ggt        816
Ser Ile Ile Gly Leu Arg Tyr Gly Val Thr Leu Gly Ile Ile Ala Gly
            260                 265                 270 gtg tta aat atg gtt ccc tat ttg gga agt ttt gtc gcc caa att cca        864
Val Leu Asn Met Val Pro Tyr Leu Gly Ser Phe Val Ala Gln Ile Pro
        275                 280                 285 gtg ttt atc tta gcg ctt gtc gca gga cct gtt atg gtt gtt aaa gtt        912
Val Phe Ile Leu Ala Leu Val Ala Gly Pro Val Met Val Val Lys Val
    290                 295                 300 gcg att gtt ttt gtt att gag caa act cta gag gga cgc ttt gtc tca        960
Ala Ile Val Phe Val Ile Glu Gln Thr Leu Glu Gly Arg Phe Val Ser
305                 310                 315                 320 cct ttg gtt tta ggt aat aaa ctt agc att cat cca att aca att atg       1008
Pro Leu Val Leu Gly Asn Lys Leu Ser Ile His Pro Ile Thr Ile Met
                325                 330                 335 ttt att tta tta acc tct gga gcg atg ttt ggt gtt tgg gga gta ttc       1056
Phe Ile Leu Leu Thr Ser Gly Ala Met Phe Gly Val Trp Gly Val Phe
            340                 345                 350 ctc agt att ccg att tat gca tct atc aaa gtt gtt gtt aaa gaa ttg       1104
Leu Ser Ile Pro Ile Tyr Ala Ser Ile Lys Val Val Val Lys Glu Leu
        355                 360                 365 ttt gat tgg tac aaa gct gtc agt ggg cta tat aca ata gat gtt gtt       1152
Phe Asp Trp Tyr Lys Ala Val Ser Gly Leu Tyr Thr Ile Asp Val Val
```

```
                370             375             380
act gaa gaa aga agt gaa gaa gtt aaa aat gtt gaa tag                    1191
Thr Glu Glu Arg Ser Glu Glu Val Lys Asn Val Glu
385             390             395
```

<210> SEQ ID NO 29
<211> LENGTH: 396
<212> TYPE: PRT
<213> ORGANISM: Streptococcus agalactiae

<400> SEQUENCE: 29

```
Val Asn Glu Ser Thr Ile Arg Lys Glu Phe Lys Ile Val Phe Lys
1               5                   10                  15

Trp Ile Leu Asn Asn Gln Ala Val Ile Ala Leu Met Ile Thr Phe Leu
            20                  25                  30

Val Phe Leu Thr Ile Phe Ile Phe Thr Lys Ile Ser Phe Met Phe Lys
            35                  40                  45

Pro Val Phe Asp Phe Leu Ala Val Leu Ile Leu Pro Leu Val Ile Ser
50                  55                  60

Gly Leu Leu Tyr Tyr Leu Leu Lys Pro Met Val Thr Phe Leu Glu Lys
65              70                  75                  80

Arg Gly Ile Lys Arg Val Thr Ala Ile Leu Ser Val Phe Thr Ile Ile
            85                  90                  95

Ile Leu Leu Leu Ile Trp Ala Met Ser Ser Phe Ile Pro Met Met Ser
            100                 105                 110

Asn Gln Leu Arg His Phe Met Glu Asp Leu Pro Ser Tyr Val Asn Lys
            115                 120                 125

Val Gln Met Glu Thr Ser Ser Phe Ile Asp His Asn Pro Trp Leu Lys
130                 135                 140

Ser Tyr Lys Gly Glu Ile Ser Ser Met Leu Ser Asn Ile Ser Ser Gln
145             150                 155                 160

Ala Val Ser Tyr Ala Glu Lys Phe Ser Lys Asn Val Leu Asp Trp Ala
            165                 170                 175

Gly Asn Leu Ala Ser Thr Val Ala Arg Val Thr Val Ala Thr Ile Met
            180                 185                 190

Ala Pro Phe Ile Leu Phe Tyr Leu Leu Arg Asp Ser Arg Asn Met Lys
            195                 200                 205

Asn Gly Phe Leu Met Val Leu Pro Thr Lys Leu Arg Gln Pro Ala Asp
            210                 215                 220

Arg Ile Leu Arg Glu Met Asn Ser Gln Met Ser Gly Tyr Val Gln Gly
225             230                 235                 240

Gln Ile Ile Val Ala Ile Thr Val Gly Val Ile Phe Ser Ile Met Tyr
                245                 250                 255

Ser Ile Ile Gly Leu Arg Tyr Gly Val Thr Leu Gly Ile Ile Ala Gly
            260                 265                 270

Val Leu Asn Met Val Pro Tyr Leu Gly Ser Phe Val Ala Gln Ile Pro
            275                 280                 285

Val Phe Ile Leu Ala Leu Val Ala Gly Pro Val Met Val Val Lys Val
            290                 295                 300

Ala Ile Val Phe Val Ile Glu Gln Thr Leu Glu Gly Arg Phe Val Ser
305             310                 315                 320

Pro Leu Val Leu Gly Asn Lys Leu Ser Ile His Pro Ile Thr Ile Met
            325                 330                 335

Phe Ile Leu Leu Thr Ser Gly Ala Met Phe Gly Val Trp Gly Val Phe
            340                 345                 350
```

-continued

```
Leu Ser Ile Pro Ile Tyr Ala Ser Ile Lys Val Val Lys Glu Leu
        355                 360                 365

Phe Asp Trp Tyr Lys Ala Val Ser Gly Leu Tyr Thr Ile Asp Val Val
    370                 375                 380

Thr Glu Glu Arg Ser Glu Glu Val Lys Asn Val Glu
385                 390                 395

<210> SEQ ID NO 30
<211> LENGTH: 1230
<212> TYPE: DNA
<213> ORGANISM: Streptococcus agalactiae
<220> FEATURE:
<221> NAME/KEY: CDS
<222> LOCATION: (1)..(1230)
<223> OTHER INFORMATION:
<221> NAME/KEY: misc_feature
<222> LOCATION: (357)..(357)
<223> OTHER INFORMATION: The 'Xaa' at location 357 stands for Thr, or
      Ile.

<400> SEQUENCE: 30 atg ttt atg gga atc cca caa tat ttc ttc tac ctt atc tta gct gtc     48
Met Phe Met Gly Ile Pro Gln Tyr Phe Phe Tyr Leu Ile Leu Ala Val
1               5                  10                  15 cta cca att tac atc ggc tta ttc ttt aag aag cgt ttt gcc tta tat    96
Leu Pro Ile Tyr Ile Gly Leu Phe Phe Lys Lys Arg Phe Ala Leu Tyr
            20                  25                  30 gag att att ttt agt cta agt ttt att gta atg atg ttg act ggt agt   144
Glu Ile Ile Phe Ser Leu Ser Phe Ile Val Met Met Leu Thr Gly Ser
        35                  40                  45 act ttt aat caa ttg aag tca cta ttg gca tac gtt gtc gga cag tct   192
Thr Phe Asn Gln Leu Lys Ser Leu Leu Ala Tyr Val Val Gly Gln Ser
    50                  55                  60 ctg cta gtt ttt atc tat aaa gct tac cgg aaa cga ttt aat cat act   240
Leu Leu Val Phe Ile Tyr Lys Ala Tyr Arg Lys Arg Phe Asn His Thr
65                  70                  75                  80 ttg gtc ttt tat gta acg gtt tgt tta tct att ttt ccg cta ttt ttg   288
Leu Val Phe Tyr Val Thr Val Cys Leu Ser Ile Phe Pro Leu Phe Leu
                85                  90                  95 gta aaa tta att cca gct ata tct gag gat ggg cat cag tca ctt ttt   336
Val Lys Leu Ile Pro Ala Ile Ser Glu Asp Gly His Gln Ser Leu Phe
            100                 105                 110 ggg ttt cta gga att tct tac ctt act ttt aga gct gtt gct atg att   384
Gly Phe Leu Gly Ile Ser Tyr Leu Thr Phe Arg Ala Val Ala Met Ile
        115                 120                 125 att gaa atg aga gac ggt gtc ttg aaa gaa ttt act tta tgg gaa ttc   432
Ile Glu Met Arg Asp Gly Val Leu Lys Glu Phe Thr Leu Trp Glu Phe
    130                 135                 140 tta aga ttt tta ctc ttc ttt cca act ttc tca agt gga cca att gat   480
Leu Arg Phe Leu Leu Phe Phe Pro Thr Phe Ser Ser Gly Pro Ile Asp
145                 150                 155                 160 cgt ttt aaa cga ttc aat gag gat tac att aat atc cca gat cga aac   528
Arg Phe Lys Arg Phe Asn Glu Asp Tyr Ile Asn Ile Pro Asp Arg Asn
                165                 170                 175 gaa ctc cta gat atg tta ggt caa gcg att cat tat ttg atg tta ggt   576
Glu Leu Leu Asp Met Leu Gly Gln Ala Ile His Tyr Leu Met Leu Gly
            180                 185                 190 ttt ctc tat aag ttt att tta gcc tat att ttt gga agt ctg att atg   624
Phe Leu Tyr Lys Phe Ile Leu Ala Tyr Ile Phe Gly Ser Leu Ile Met
        195                 200                 205 cct cct cta aaa gaa tta gcg cta gaa cag ggt ggt gtg ttt aat tgg   672
```

```
                Pro Pro Leu Lys Glu Leu Ala Leu Glu Gln Gly Gly Val Phe Asn Trp
                        210                 215                 220 cca aca ctt ggg gtt atg tat gcc ttt ggt ttt gat ttg ttc ttt gat           720
Pro Thr Leu Gly Val Met Tyr Ala Phe Gly Phe Asp Leu Phe Phe Asp
225                 230                 235                 240 ttt gca ggt tac aca atg ttt gcg ttg gct att tct aac cta atg ggg           768
Phe Ala Gly Tyr Thr Met Phe Ala Leu Ala Ile Ser Asn Leu Met Gly
                245                 250                 255 att aag tct ccg att aac ttt gac aaa cct ttc aaa tca cgc gac cta           816
Ile Lys Ser Pro Ile Asn Phe Asp Lys Pro Phe Lys Ser Arg Asp Leu
            260                 265                 270 aaa gaa ttt tgg aat aga tgg cat atg agc ctt tct ttc tgg ttt aga           864
Lys Glu Phe Trp Asn Arg Trp His Met Ser Leu Ser Phe Trp Phe Arg
        275                 280                 285 gac ttt gtt ttc atg agg ctt gtt aag ctt tta gtt aaa aat aaa gtt           912
Asp Phe Val Phe Met Arg Leu Val Lys Leu Leu Val Lys Asn Lys Val
    290                 295                 300 ttt aaa aac cgt aat gtt act tca agt gta gct tat att atc aat atg           960
Phe Lys Asn Arg Asn Val Thr Ser Ser Val Ala Tyr Ile Ile Asn Met
305                 310                 315                 320 ctt ctt atg gga ttc tgg cat ggg tta act tgg tac tat ata gcc tat          1008
Leu Leu Met Gly Phe Trp His Gly Leu Thr Trp Tyr Tyr Ile Ala Tyr
                325                 330                 335 ggt ctc ttt cat ggg att ggc cta gtt att aat gac gct tgg gta cgt          1056
Gly Leu Phe His Gly Ile Gly Leu Val Ile Asn Asp Ala Trp Val Arg
                340                 345                 350 aag aag aaa aat ayt aat aaa gaa aga aga ttg gct aaa aaa cca ctt          1104
Lys Lys Lys Asn Xaa Asn Lys Glu Arg Arg Leu Ala Lys Lys Pro Leu
            355                 360                 365 tta cca gaa aac aaa tgg act tat gct ttg ggt gtc ttc atc acc ttt          1152
Leu Pro Glu Asn Lys Trp Thr Tyr Ala Leu Gly Val Phe Ile Thr Phe
        370                 375                 380 aat gta gtt atg ttt tct ttc ttg att ttt tca gga ttt tta gat ctt          1200
Asn Val Val Met Phe Ser Phe Leu Ile Phe Ser Gly Phe Leu Asp Leu
385                 390                 395                 400 ttg tgg ttc cca caa ccg cat aac aaa taa                                  1230
Leu Trp Phe Pro Gln Pro His Asn Lys
                405
```

<210> SEQ ID NO 31
<211> LENGTH: 409
<212> TYPE: PRT
<213> ORGANISM: Streptococcus agalactiae
<220> FEATURE:
<221> NAME/KEY: misc_feature
<222> LOCATION: (357)..(357)
<223> OTHER INFORMATION: The 'Xaa' at location 357 stands for Thr, or Ile.

<400> SEQUENCE: 31

```
Met Phe Met Gly Ile Pro Gln Tyr Phe Phe Tyr Leu Ile Leu Ala Val
1               5                   10                  15

Leu Pro Ile Tyr Ile Gly Leu Phe Phe Lys Lys Arg Phe Ala Leu Tyr
                20                  25                  30

Glu Ile Ile Phe Ser Leu Ser Phe Ile Val Met Met Leu Thr Gly Ser
            35                  40                  45

Thr Phe Asn Gln Leu Lys Ser Leu Leu Ala Tyr Val Val Gly Gln Ser
        50                  55                  60

Leu Leu Val Phe Ile Tyr Lys Ala Tyr Arg Lys Arg Phe Asn His Thr
65                  70                  75                  80
```

```
Leu Val Phe Tyr Val Thr Val Cys Leu Ser Ile Phe Pro Leu Phe Leu
                 85                  90                  95

Val Lys Leu Ile Pro Ala Ile Ser Glu Asp Gly His Gln Ser Leu Phe
                100                 105                 110

Gly Phe Leu Gly Ile Ser Tyr Leu Thr Phe Arg Ala Val Ala Met Ile
                115                 120                 125

Ile Glu Met Arg Asp Gly Val Leu Lys Glu Phe Thr Leu Trp Glu Phe
130                 135                 140

Leu Arg Phe Leu Leu Phe Phe Pro Thr Phe Ser Ser Gly Pro Ile Asp
145                 150                 155                 160

Arg Phe Lys Arg Phe Asn Glu Asp Tyr Ile Asn Ile Pro Asp Arg Asn
                165                 170                 175

Glu Leu Leu Asp Met Leu Gly Gln Ala Ile His Tyr Leu Met Leu Gly
                180                 185                 190

Phe Leu Tyr Lys Phe Ile Leu Ala Tyr Ile Phe Gly Ser Leu Ile Met
                195                 200                 205

Pro Pro Leu Lys Glu Leu Ala Leu Glu Gln Gly Gly Val Phe Asn Trp
                210                 215                 220

Pro Thr Leu Gly Val Met Tyr Ala Phe Gly Phe Asp Leu Phe Phe Asp
225                 230                 235                 240

Phe Ala Gly Tyr Thr Met Phe Ala Leu Ala Ile Ser Asn Leu Met Gly
                245                 250                 255

Ile Lys Ser Pro Ile Asn Phe Asp Lys Pro Phe Lys Ser Arg Asp Leu
                260                 265                 270

Lys Glu Phe Trp Asn Arg Trp His Met Ser Leu Ser Phe Trp Phe Arg
                275                 280                 285

Asp Phe Val Phe Met Arg Leu Val Lys Leu Leu Val Lys Asn Lys Val
290                 295                 300

Phe Lys Asn Arg Asn Val Thr Ser Ser Val Ala Tyr Ile Ile Asn Met
305                 310                 315                 320

Leu Leu Met Gly Phe Trp His Gly Leu Thr Trp Tyr Tyr Ile Ala Tyr
                325                 330                 335

Gly Leu Phe His Gly Ile Gly Leu Val Ile Asn Asp Ala Trp Val Arg
                340                 345                 350

Lys Lys Lys Asn Xaa Asn Lys Glu Arg Arg Leu Ala Lys Lys Pro Leu
                355                 360                 365

Leu Pro Glu Asn Lys Trp Thr Tyr Ala Leu Gly Val Phe Ile Thr Phe
370                 375                 380

Asn Val Val Met Phe Ser Phe Leu Ile Phe Ser Gly Phe Leu Asp Leu
385                 390                 395                 400

Leu Trp Phe Pro Gln Pro His Asn Lys
                405

<210> SEQ ID NO 32
<211> LENGTH: 100
<212> TYPE: DNA
<213> ORGANISM: Streptococcus agalactiae
<220> FEATURE:
<221> NAME/KEY: CDS
<222> LOCATION: (1)..(99)
<223> OTHER INFORMATION:

<400> SEQUENCE: 32 atg aat aaa ata acg aca tta tca acc atc gcc ctg act tta atg ctt     48
Met Asn Lys Ile Thr Thr Leu Ser Thr Ile Ala Leu Thr Leu Met Leu
1               5                   10                  15
```

```
tgc gtt gga tgt tct gcc aat aaa gat aat caa aaa act aaa act gag    96
Cys Val Gly Cys Ser Ala Asn Lys Asp Asn Gln Lys Thr Lys Thr Glu
            20                  25                  30 gat c                                                              100
Asp
```

<210> SEQ ID NO 33
<211> LENGTH: 33
<212> TYPE: PRT
<213> ORGANISM: Streptococcus agalactiae

<400> SEQUENCE: 33

```
Met Asn Lys Ile Thr Thr Leu Ser Thr Ile Ala Leu Thr Leu Met Leu
1               5                   10                  15

Cys Val Gly Cys Ser Ala Asn Lys Asp Asn Gln Lys Thr Lys Thr Glu
            20                  25                  30

Asp
```

<210> SEQ ID NO 34
<211> LENGTH: 654
<212> TYPE: DNA
<213> ORGANISM: Streptococcus agalactiae
<220> FEATURE:
<221> NAME/KEY: CDS
<222> LOCATION: (1)..(654)
<223> OTHER INFORMATION:

<400> SEQUENCE: 34

```
gat cga ggc tat caa gaa gca atg gct aaa cta agg aaa act tac ggc    48
Asp Arg Gly Tyr Gln Glu Ala Met Ala Lys Leu Arg Lys Thr Tyr Gly
1               5                   10                  15 gaa tat ggt tta ggg gtt tct aca gga tta gat tta cct gaa tca gaa    96
Glu Tyr Gly Leu Gly Val Ser Thr Gly Leu Asp Leu Pro Glu Ser Glu
            20                  25                  30 ggt tat gta cct gga aaa tac agc tta gga aca act cta atg gaa tcg    144
Gly Tyr Val Pro Gly Lys Tyr Ser Leu Gly Thr Thr Leu Met Glu Ser
        35                  40                  45 ttc ggt cag tat gat gcc tat aca cca atg caa ctt ggt cag tat atc    192
Phe Gly Gln Tyr Asp Ala Tyr Thr Pro Met Gln Leu Gly Gln Tyr Ile
    50                  55                  60 tca act att gcg aat aat ggg aat cgt tta gca cct cac gtg gtt tca    240
Ser Thr Ile Ala Asn Asn Gly Asn Arg Leu Ala Pro His Val Val Ser
65                  70                  75                  80 gat atc tat gaa ggg aat gat tct aat aag ttc gct caa ttg gtt cgt    288
Asp Ile Tyr Glu Gly Asn Asp Ser Asn Lys Phe Ala Gln Leu Val Arg
                85                  90                  95 tca atc act cct aaa aca cta aat aag ata gct atc tca gat caa gag    336
Ser Ile Thr Pro Lys Thr Leu Asn Lys Ile Ala Ile Ser Asp Gln Glu
            100                 105                 110 tta gcc att att caa gaa ggt ttt tat aac gtt gtc aat agt gga agt    384
Leu Ala Ile Ile Gln Glu Gly Phe Tyr Asn Val Val Asn Ser Gly Ser
        115                 120                 125 ggc tat gca act ggt acg tca atg agg ggg aat gtg aca acc att agy    432
Gly Tyr Ala Thr Gly Thr Ser Met Arg Gly Asn Val Thr Thr Ile Ser
    130                 135                 140 ggt aaa act ggt acc gct gaa aca ttt gct aaa aat ata aat gga caa    480
Gly Lys Thr Gly Thr Ala Glu Thr Phe Ala Lys Asn Ile Asn Gly Gln
145                 150                 155                 160 aca gtt tct acc tac aac tta aac gct att gcc tac gat act aat cgt    528
Thr Val Ser Thr Tyr Asn Leu Asn Ala Ile Ala Tyr Asp Thr Asn Arg
                165                 170                 175
```

-continued

```
aaa ata gca gta gcg gta atg tat ccg cat gtt aca act gat aca aca    576
Lys Ile Ala Val Ala Val Met Tyr Pro His Val Thr Thr Asp Thr Thr
        180                 185                 190 aaa tcc cat caa tta gtt gca cga gat atg att gat caa tat att tca    624
Lys Ser His Gln Leu Val Ala Arg Asp Met Ile Asp Gln Tyr Ile Ser
        195                 200                 205 cag tca cag gac aat aag aga gga cat tga                            654
Gln Ser Gln Asp Asn Lys Arg Gly His
    210                 215
```

<210> SEQ ID NO 35
<211> LENGTH: 217
<212> TYPE: PRT
<213> ORGANISM: Streptococcus agalactiae

<400> SEQUENCE: 35

```
Asp Arg Gly Tyr Gln Glu Ala Met Ala Lys Leu Arg Lys Thr Tyr Gly
1               5                   10                  15

Glu Tyr Gly Leu Gly Val Ser Thr Gly Leu Asp Leu Pro Glu Ser Glu
            20                  25                  30

Gly Tyr Val Pro Gly Lys Tyr Ser Leu Gly Thr Thr Leu Met Glu Ser
        35                  40                  45

Phe Gly Gln Tyr Asp Ala Tyr Thr Pro Met Gln Leu Gly Gln Tyr Ile
    50                  55                  60

Ser Thr Ile Ala Asn Asn Gly Asn Arg Leu Ala Pro His Val Val Ser
65                  70                  75                  80

Asp Ile Tyr Glu Gly Asn Asp Ser Asn Lys Phe Ala Gln Leu Val Arg
                85                  90                  95

Ser Ile Thr Pro Lys Thr Leu Asn Lys Ile Ala Ile Ser Asp Gln Glu
            100                 105                 110

Leu Ala Ile Ile Gln Glu Gly Phe Tyr Asn Val Val Asn Ser Gly Ser
        115                 120                 125

Gly Tyr Ala Thr Gly Thr Ser Met Arg Gly Asn Val Thr Thr Ile Ser
    130                 135                 140

Gly Lys Thr Gly Thr Ala Glu Thr Phe Ala Lys Asn Ile Asn Gly Gln
145                 150                 155                 160

Thr Val Ser Thr Tyr Asn Leu Asn Ala Ile Ala Tyr Asp Thr Asn Arg
                165                 170                 175

Lys Ile Ala Val Ala Val Met Tyr Pro His Val Thr Thr Asp Thr Thr
            180                 185                 190

Lys Ser His Gln Leu Val Ala Arg Asp Met Ile Asp Gln Tyr Ile Ser
        195                 200                 205

Gln Ser Gln Asp Asn Lys Arg Gly His
    210                 215
```